(12) United States Patent
Matsumoto et al.

(10) Patent No.: US 7,726,190 B2
(45) Date of Patent: Jun. 1, 2010

(54) DEVICE, METHOD AND PROGRAM FOR INSPECTING MICROSTRUCTURE

(75) Inventors: Toshiyuki Matsumoto, Amagasaki (JP); Naoki Ikeuchi, Amagasaki (JP); Masami Yakabe, Amagasaki (JP); Keiichi Enjoji, Tokyo (JP); Masato Hayashi, Amagasaki (JP)

(73) Assignee: Tokyo Electron Limited, Tokyo (JP)

( * ) Notice: Subject to any disclaimer, the term of this patent is extended or adjusted under 35 U.S.C. 154(b) by 276 days.

(21) Appl. No.: 11/885,432

(22) PCT Filed: Mar. 2, 2006

(86) PCT No.: PCT/JP2006/303996

§ 371 (c)(1),
(2), (4) Date: Aug. 31, 2007

(87) PCT Pub. No.: WO2006/093232

PCT Pub. Date: Sep. 8, 2006

(65) Prior Publication Data

US 2008/0190206 A1    Aug. 14, 2008

(30) Foreign Application Priority Data

Mar. 3, 2005    (JP) ............................... 2005-059061

(51) Int. Cl.
*G01N 29/00* (2006.01)
*H01L 41/00* (2006.01)

(52) U.S. Cl. .............................. 73/602; 73/584; 73/662; 310/334

(58) Field of Classification Search .................... 73/584, 73/649, 651, 655, 658, 662, 663; 310/334, 310/336, 338, 357–358

See application file for complete search history.

(56) References Cited

U.S. PATENT DOCUMENTS 6,651,504 B1 *    11/2003    Datskos ....................... 73/651

(Continued)

FOREIGN PATENT DOCUMENTS

JP    51-20892    2/1976

(Continued)

OTHER PUBLICATIONS

European Search Report dated Feb. 24, 2009.

(Continued)

*Primary Examiner*—J M Saint Surin
(74) *Attorney, Agent, or Firm*—Finnegan, Henderson, Farabow, Garrett & Dunner, LLP

(57) ABSTRACT

A speaker unit has a plurality of sound sources each outputting a sound wave. The compressional, sound wave output from the speaker unit arrives, or vibrates air, which moves a movable part of a three-axis acceleration sensor, or a microstructure of a chip to be tested TP. As the movable part thus moves, a value in resistance accordingly varies, and such variation is measured as based on an output voltage provided via a probe. A control unit determines a property of the three-axis acceleration sensor from a value in property as measured or measurement data. Furthermore, the plurality of sound sources can be spaced by a pitch of a predetermined value set as based on their difference in the distance to the movable part of the three-axis acceleration sensor and the wavelength of the test wave to apply a composite test wave to the movable part such that the composite sound wave's composite sound field is maximized.

12 Claims, 25 Drawing Sheets

U.S. PATENT DOCUMENTS

| | | | |
|---|---|---|---|
| 6,901,802 B2* | 6/2005 | Datskos | 73/651 |
| 7,348,788 B2* | 3/2008 | Yakabe et al. | 324/754 |
| 7,383,732 B2* | 6/2008 | Okumura et al. | 73/602 |
| 2002/0189357 A1 | 12/2002 | Lai et al. | |
| 2004/0066516 A1 | 4/2004 | Deason et al. | |
| 2005/0253571 A1* | 11/2005 | Frank et al. | 324/76.11 |
| 2007/0238213 A1* | 10/2007 | Yamaguchi et al. | 438/48 |
| 2009/0095095 A1* | 4/2009 | Hayashi et al. | 73/865.8 |

FOREIGN PATENT DOCUMENTS

| | | |
|---|---|---|
| JP | 61-207964 | 9/1986 |
| JP | 2-67956 | 3/1990 |
| JP | 5-34371 | 2/1993 |
| JP | 9-33500 | 2/1997 |
| JP | 11-2643 | 1/1999 |
| JP | 11-002643 A | 1/1999 |

OTHER PUBLICATIONS

"Present Status of MEMS Technology and Related Issues," Technology Research Report No. 3, (Ministry of Economy, Trade and Industry, Industrial Science and Technology Policy and Environment Bureau, Technology Research and Information Office and Manufacturing Industries Bureau, Industrial Machinery Division), Mar. 28, 2003.

S. Sanuki, eta l., "The Influence of Stack Position on Sound Wave of Thermoacoustic Engine", The Japan Society of Mechanical Engineers Hokkaido Shibu Dai 42 Kai Koenkai Gaiyoshu, pp. 60-61 (2002).

T. Yazaki, et al., "Measurement of sound generation in thermoacoustic oscillations", Proc. R. Soc. Lond. A., vol. 454, pp. 2113-2122 (1998).

O. Tabata, "Testing of Thin Film Mechanical Property for Micro Electro Mechanical Systems", The Japan Society of Mechanical Engineers 1999 Nendo Nenji taikai Koen Ronbunshu, pp. 496-497 (1999).

K. Yasuda, "Mechanical Acoustics", Corona Publishing Co., Ltd., (2004) pp. 11-16 and 106-116.

Korean Office Action dated May 6, 2009.

* cited by examiner

A: RESONANT FREQUENCY RANGE
B: NON-RESONANT FREQUENCY RANGE

N=64, d/λ =2.0

Angle[degree]
d/λ=0.5

FIG.20
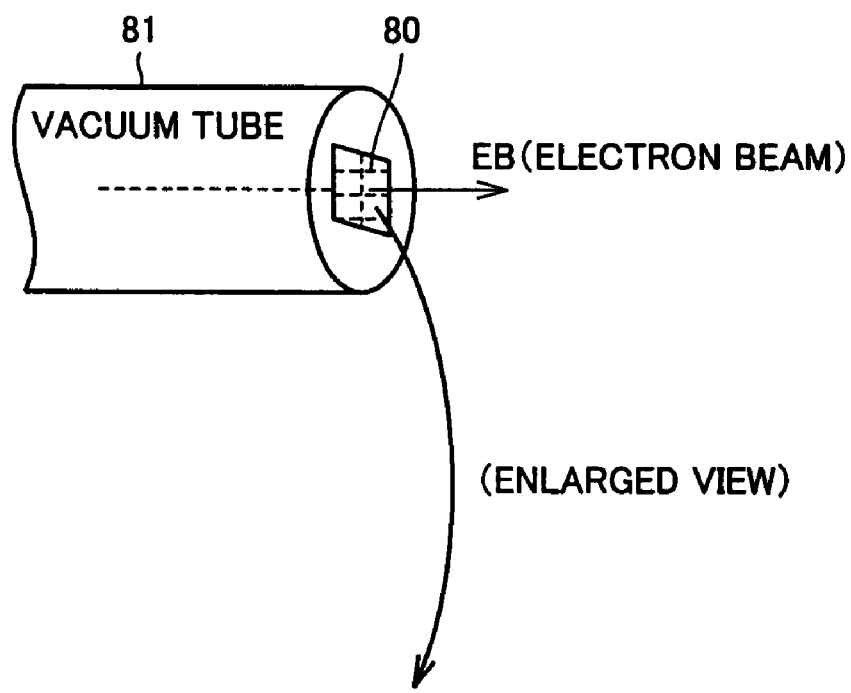
(ENLARGED VIEW)
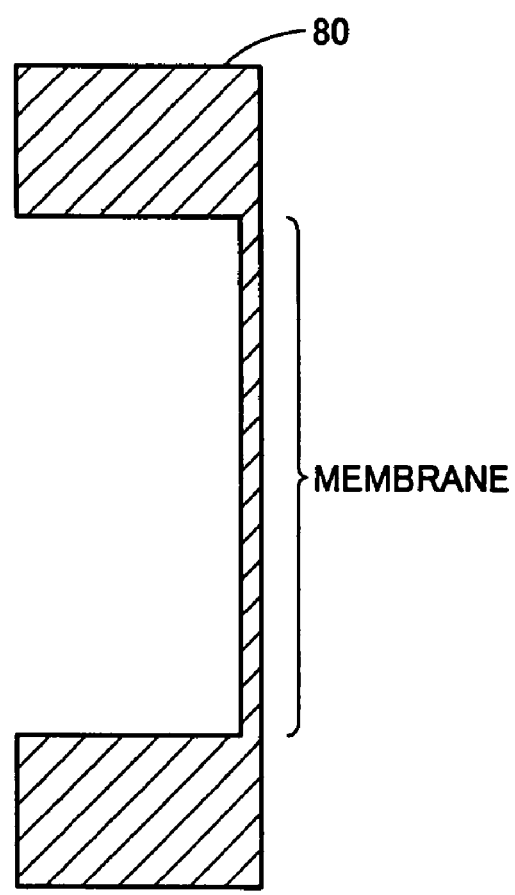

90

DEVICE, METHOD AND PROGRAM FOR INSPECTING MICROSTRUCTURE

TECHNICAL FIELD

The present invention relates to a device, a method and a program for inspecting microstructure, such as MEMS (Micro Electro Mechanical Systems).

BACKGROUND ART

In recent years, MEMS which is a device where various functions, such as mechanical, electronic, optical and chemical functions, are integrated, particularly using a semiconductor microscopic processing or the like, have drawn attention. In accordance with MEMS technologies that have been put into practice so far, MEMS devices have been mounted as various types of sensors for, for example, automobiles and medical purposes, on micro sensors such as acceleration sensors, pressure sensors, air flow sensors, and the like. In addition, such MEMS technologies have been adopted in an inkjet printer head, and thereby, an increase in the number of nozzles for spewing an ink and precise spewing of an ink have become possible, making it possible to achieve an increase in the quality of pictures and an increase in the speed of printing. Furthermore, a micro mirror array or the like that is used in a reflection type projector is also known as a general MEMS device.

In addition, a variety of sensors and actuators will be developed by utilizing MEMS technologies in the future, and thereby, it is expected that application to optical communications and mobile apparatuses, application to peripheral apparatuses of computers, and application to biotechnological analysis and power sources for portable apparatuses will broaden. A variety of MEMS technologies are introduced in Technology Research Report Number 3 (issued by the Manufacturing Industry Bureau Industrial Machinery Section of the Ministry of Economy, Trade and Industry, Technology Environment Bureau Technology Research Division, on Mar. 28, 2003) under the agenda of state of the art and problems concerning MEMS.

Meanwhile, a system for appropriately inspecting MEMS devices is becoming more and more important, because of the microstructure thereof, as MEMS devices develop. Though the property of devices have been evaluated by rotating the devices after packaging or by using means such as vibration according to the prior art, it will become possible to increase the yield and reduce the manufacturing cost by detecting defects as a result of appropriate inspection carried out in the initial step, where the devices are in the state of wafers, after the application of a microscopic processing.

In Japanese Laid-Open Patent Publication No. 05-034371 (Patent Document 1), an inspection system for detecting the resistance value of an acceleration sensor that changes by blowing air against the acceleration sensor formed on a wafer, and thereby, for determining the property of the acceleration sensor, has been proposed as an example.

Patent Document 1: Japanese Patent Laying-open No. 5-34371

Non-Patent Document 1: Technology Research Report Number 3 (issued by the Manufacturing Industry Bureau Industrial Machinery Section of the Ministry of Economy, Trade and Industry, Technology Environment Bureau Technology Research Division, on Mar. 28, 2003)

DISCLOSURE OF THE INVENTION

Problems to be Solved by the Invention

In general, a structure having a microscopic movable part, such as an acceleration sensor, is a device of which the response property change in accordance with a microscopic movement. Accordingly, it is necessary to carry out inspection with high precision, in order to evaluate these property. Though the property of an acceleration sensor must be evaluated by carrying out microscopic adjustment, even in the case where a device is changed by blowing air to the device as shown in the above-described gazette, it is extremely difficult to carry out inspection with high precision by controlling the amount of gas flow, and at the same time uniformly blowing a gas against the device, and a complex, expensive tester must be provided, even when such inspection is implemented.

Furthermore for blowing air it is difficult to provide the air with directivity to blow the air to a particular position to perform inspection with high precision.

The present invention has been made in order to solve the above-described problem, and an object thereof is to provide a device, method, program for inspecting a structure having a microscopic movable part with high precision and in a simple system.

Means for Solving the Problems

The present microstructure inspection device evaluates a property of at least one microstructure having a movable part formed on a substrate. The present microstructure inspection device includes a sound wave generation unit outputting a sound wave to the microstructure in a test. The sound wave generation unit includes a plurality of sound sources each outputting the sound wave, and an adjustment unit for adjusting a composite wave to serve as a predetermined test sound wave, the composite wave being composed of sound waves output from the plurality of sound sources. The present microstructure inspection device further includes an evaluation unit detecting how the movable part of the microstructure moves in response to the test sound wave, for evaluating the property of the microstructure from how the movable part moves, as detected.

Preferably the plurality of sound sources are arranged to each have a difference in the distance to the movable part to be an integer multiple of a wavelength of the sound wave.

Preferably the microstructure inspection device is set such that the plurality of sound sources each output the sound wave to arrive at the movable part concurrently.

In particular, the plurality of sound sources are equally spaced and driven at times, respectively, each delayed by a predetermined period of time, to output the sound wave.

Preferably the microstructure corresponds to at least one of an acceleration sensor and an angular rate sensor.

In particular, the acceleration sensor and the angular rate sensor correspond to a multi-axial acceleration sensor and a multi-axial angular rate sensor, respectively.

Preferably the adjustment unit includes a position control unit operative in response to an instruction to control the plurality of sound sources positionally and the sound sources are each movable.

Preferably the plurality of sound sources are provided in an array and the adjustment unit includes a switch unit for controlling the plurality of sound sources to turn on/off. The plurality of sound sources arranged in the array are selected as the switch unit switches in response to an instruction.

Preferably the sound sources are each configured of a thermal acoustic engine including a thermally conductive substrate, a thermal insulation layer formed of a nanocrystalline silicon layer provided on one surface of the substrate, and a heating element receiving a current including an alternate-current component to be electrically driven to exchange heat with air therearound to generate a sound wave.

Preferably the plurality of sound sources are formed on the thermally conductive, single substrate in a semiconductor process collectively.

The present method of inspecting a microstructure evaluates a property of at least one microstructure having a movable part formed on a substrate. The method includes the steps of: adjusting a composite wave to be a predetermined test sound wave for output, the composite wave being composed of sound waves output from a plurality of sound sources in a test; and detecting how the movable part of the microstructure moves in response to the test sound wave, and evaluating the property of the microstructure from how the movable part moves, as detected.

The present microstructure inspection program evaluates a property of at least one microstructure having a movable part formed on a substrate. The program causes a computer to perform a method of inspecting the microstructure, including the steps of: adjusting a composite wave to be a predetermined test sound wave for output, the composite wave being composed of sound waves output from a plurality of sound sources in a test; and detecting how the movable part of the microstructure moves in response to the test sound wave, and evaluating the property of the microstructure from how the movable part moves, as detected.

Effects of the Invention

The present microstructure inspection device, method and program applies a test sound wave to a microstructure to detect how a movable part of the microstructure moves, and evaluate a property thereof The movable part of the microstructure is moved by air vibrated by a sound wave, which is a compressional wave, and a simple system can be employed to inspect the microstructure.

BRIEF DESCRIPTION OF THE DRAWINGS

FIG. 20 is a diagram for illustrating a case where an illumination window of an electron beam illuminator has a membrane structure.

Figure 1:
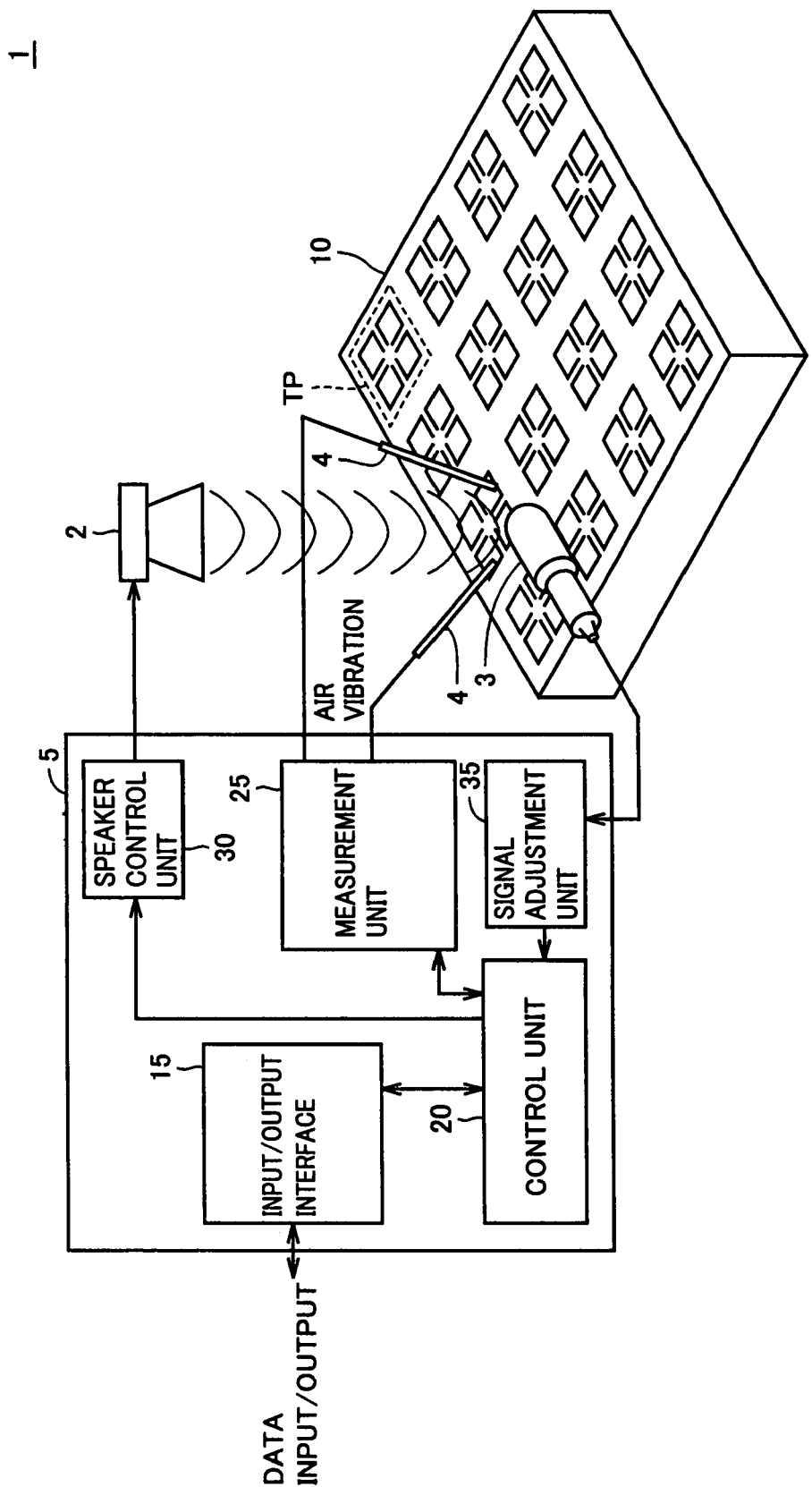
FIG. 1 is a schematic configuration diagram showing a system for inspecting a microstructure according to a first embodiment of the present invention.

DESCRIPTION OF THE REFERENCE SIGNS 1, 1#, 1#a: inspection system; 2, ARY, ARY#: speaker unit; 3: microphone; 4: probe needle; 5, 5#, 5#a: tester; 6: position control unit; 10, 40: substrate; 15: input/output interface; 20: control unit; 25: measurement unit; 30: speaker control unit; 35: signal adjustment unit; 100: sound source select unit; SPU: sub speaker unit.

BEST MODES FOR CARRYING OUT THE INVENTION

In the following, the embodiments of this invention are described in detail, with reference to the drawings. Here, the same symbols are attached to parts that are the same as or corresponding to those in the drawings, and the descriptions thereof are not repeated.

First Embodiment

FIG. 1 is a schematic configuration diagram showing a system for inspecting a microstructure according to a first embodiment of the present invention.

With reference to FIG. 1, the present invention in the first embodiment provides inspection system 1 provided with a tester (inspection device) 5 and a substrate 10 where a number of chips TP of microstructure having microscopic movable parts are formed.

In the present example, a three-axis acceleration sensor which has multiple axes is cited and described as an example of a microstructure that is to be tested.

Tester 5 is provided with a speaker unit 2 for outputting sound wave which is compression wave, an input/output interface 15 for transferring input/output data between the outside and the inside of the tester, a control unit 20 for controlling the entirety of tester 5, probe needles 4 which are used to make contact with the test object, a speaker control unit 30 for controlling speaker unit 2 in response to an instruction from control unit 20, a microphone 3 for detecting sound from the outside, and a signal adjustment unit 35 for converting the sound wave that has been detected by microphone 3 into a voltage signal, and furthermore, for amplifying the voltage signal which is then outputted to control unit 20. Here, it is possible to place microphone 3 in the vicinity of the test object. Note that, as will be described later, speaker unit 2 is configured of a plurality of speakers (or sound sources).

First, the three-axis acceleration sensor of a microstructure which is the test object is described, before describing the inspection method according to the present embodiment.

Figure 2:
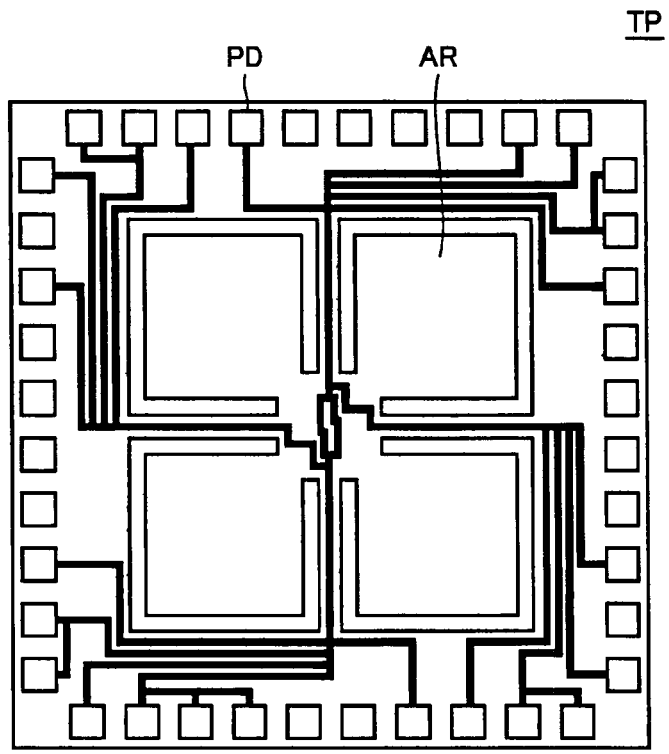
FIG. 2 is a diagram showing a device of a three-axis acceleration sensor as viewed from above.

FIG. 2 is a diagram showing a device of a three-axis acceleration sensor as viewed from above.

As shown in FIG. 2, a plurality of pads PD are placed around the periphery of a chip TP that is formed on a substrate 10. In addition, metal wires for transmitting an electrical signal to a pad or for transmitting an electrical signal from a pad are provided. Furthermore, four proof masses AR that form a four-leafed clover shape are placed in the center portion.

Figure 3:
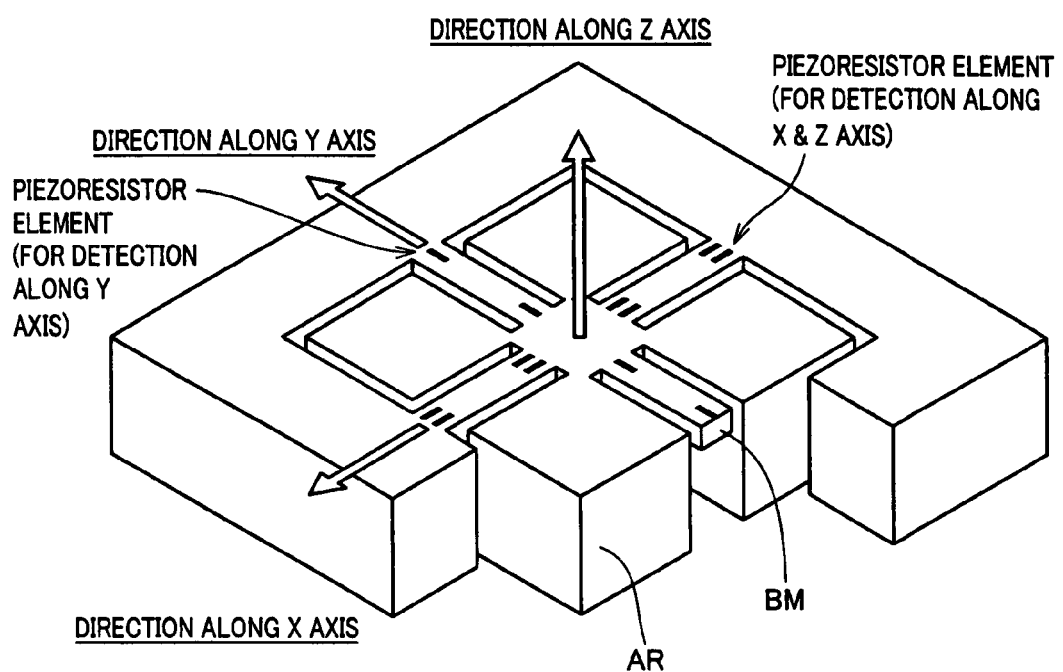
FIG. 3 is a schematic diagram showing the three-axis acceleration sensor.

FIG. 3 is a schematic diagram showing the three-axis acceleration sensor.

With reference to FIG. 3, this three-axis acceleration sensor is of a piezoresistive element type, and a piezoresistive element which is a detection element is provided as resistance of diffused region. This piezoresistive element type acceleration sensor can be made using an inexpensive IC process, and the sensitivity is not lowered, even in the case where the resistor element that is a detection element is formed so as to be small, and therefore, this acceleration sensor is advantageous for miniaturization and reduction in cost.

As a specific configuration, proof masses AR at the center have structures that are supported by four beams BM in a concrete configuration. Beams BM are formed so as to be perpendicular to each other in the two axial directions X and Y, where four piezoresistive elements are provided for each axis. Four piezoresistive elements for detection in the direction of the Z axis are provided on the side of the piezoresistive elements for detection in the direction of the X axis. The form of the upper surface of proof masses AR is in four-leafed clover form, and proof masses AR are linked to beams BM in the center portion. It becomes possible to implement a highly sensitive acceleration sensor which is compact, even though the size of proof masses AR is increased and at the same time the length of the beams is increased, by adopting this four-leafed clover type structure.

The sensing mechanism of the three-axis acceleration sensor of this piezoresistive element type provides a mechanism where beams BM are deformed when the proof masses receive acceleration (force of inertia) and the acceleration is detected due to a change in the resistance values of the piezoresistive elements which have been formed on the surface of the beams. In addition, this output of the sensor is set to be taken out in the configuration as the output of the below described Wheatstone's bridge, where three axes are independently associated.

Figure 4:
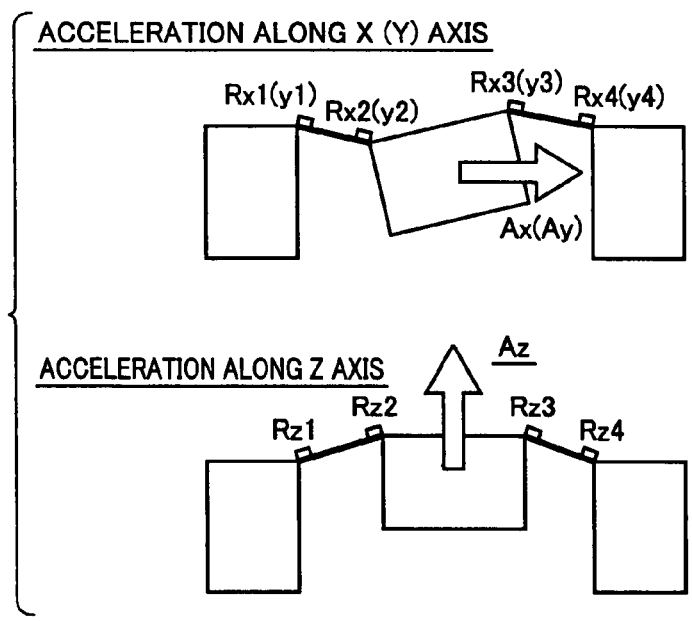
FIG. 4 is a conceptual diagram for illustrating proof masses and deformation of beams in the case where an acceleration is applied in the direction of each axis.

FIG. 4 is a conceptual diagram for illustrating proof masses and deformation of beams in the case where an acceleration is applied in the direction of each axis.

As shown in FIG. 4, a piezoresistive element has property where the resistance value thereof changes due to a warp that has been caused (piezoresistive element effect), in a manner where the resistance value increases in the case of a warp caused by stretching and the resistance value decreases in the case of a warp caused by compression. In the present embodiment, piezoresistive elements for detection in the direction of the X axis Rx1 to Rx4, piezoresistive elements for detection in the direction of the Y axis Ry1 to Ry4, and piezoresistive elements for detection in the direction of the Z axis Rz1 to Rz4 are shown as examples.

Figure 5:
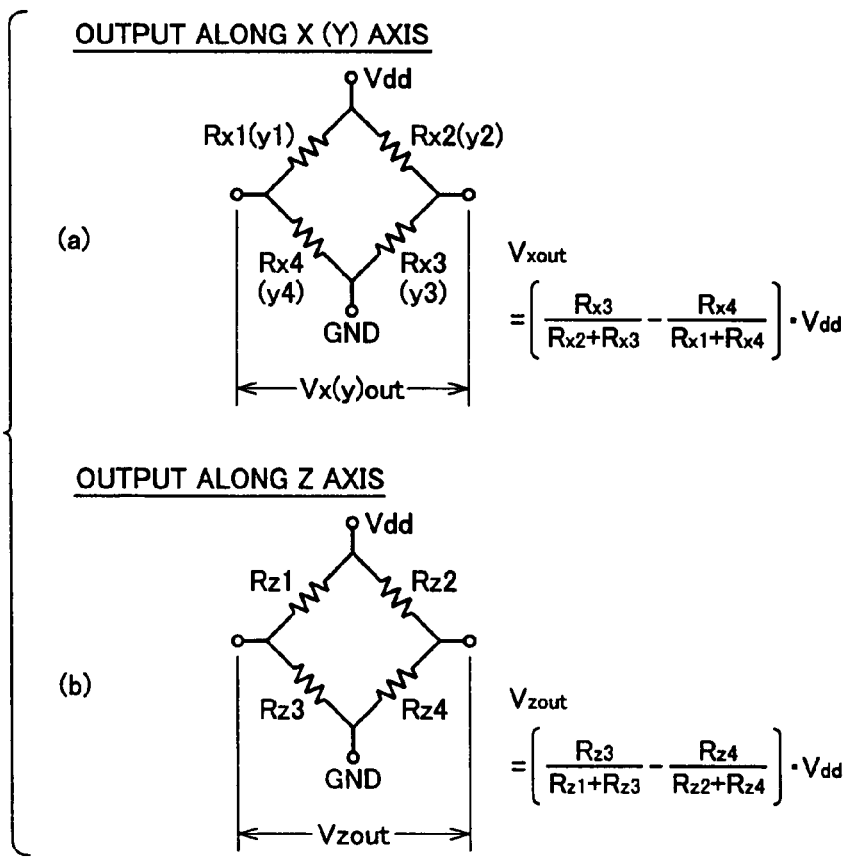
FIG. 5 is circuit configuration diagrams showing Wheatstone's bridges provided for each axis.

FIG. 5 is circuit configuration diagrams showing Wheatstone's bridges provided for each axis.

FIG. 5(a) is a circuit configuration diagram of a Wheatstone's bridge along the X (Y) axis. The output voltages of the X axis and the Y axis are assumed to be Vxout and Vyout, respectively.

FIG. 5(b) is a circuit configuration diagram of a Wheatstone's bridge along the Z axis. The output voltage of the Z axis is assumed to be Vzout.

As described above, the resistance values of the four piezoresistive elements along each axis change due to a warp that has been caused, and on the basis of this change, the circuit that is formed as a Wheatstone's bridge by each piezoresistive element along, for example, the X axis and the Y axis, detects the acceleration component along each axis of the output as an independent, separate output voltage. Here, the above-described metal wires and the like, as shown in FIG. 2, are linked so that a circuit as described above is formed, and an output voltage for each axis is detected from a predetermined pad in the configuration.

In addition, this three-axis acceleration sensor can detect the DC component of acceleration, and therefore, it is possible to use this three-axis acceleration sensor as an inclination angle sensor for detecting acceleration in the gravity, that is, as an angular rate sensor.

Figure 6:
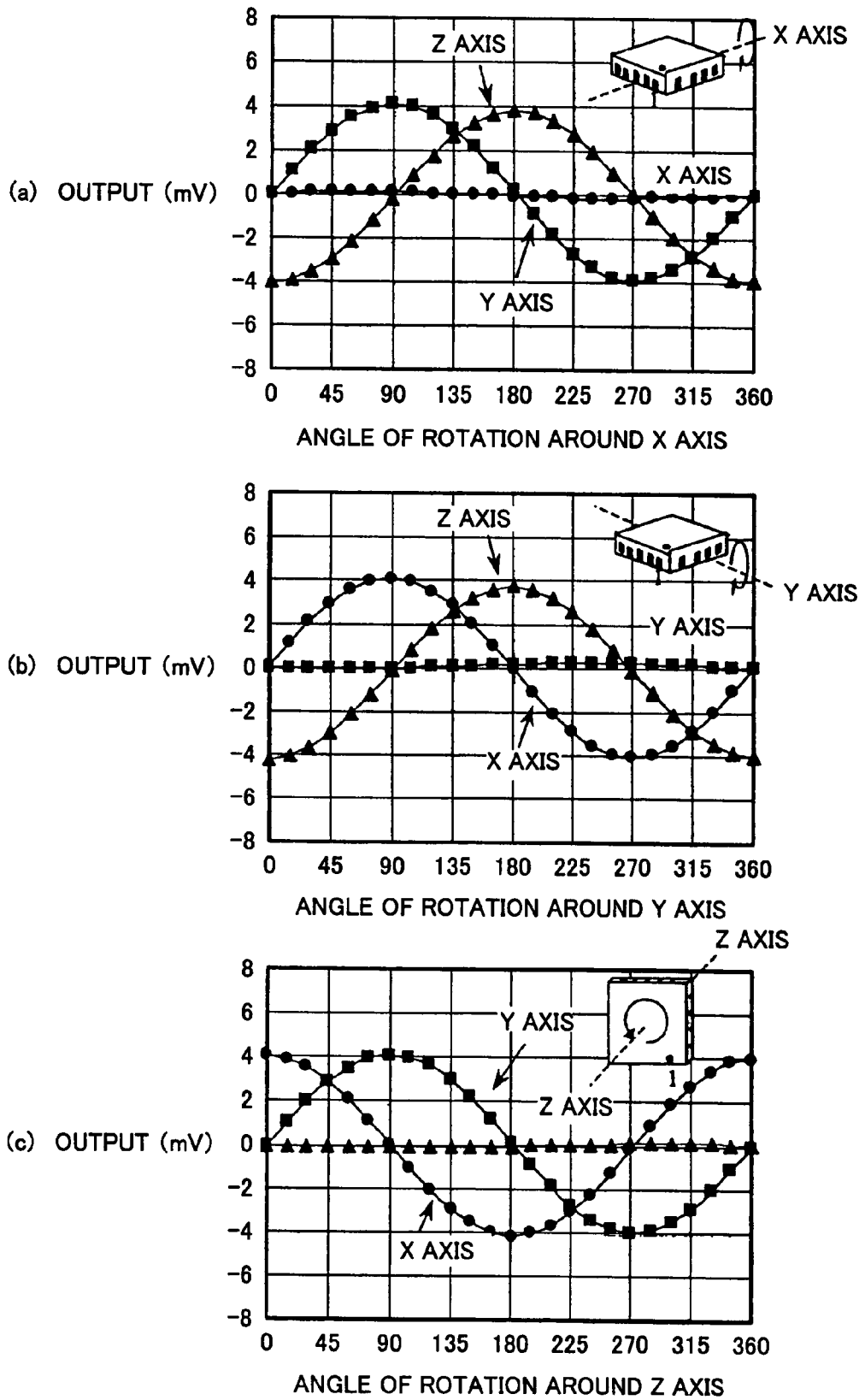
FIG. 6 is graphs for describing an output response relative to an inclination angle of a three-axis acceleration sensor.

FIG. 6 is graphs for describing an output response relative to an inclination angle of a three-axis acceleration sensor.

As shown in FIG. 6, a sensor is rotated around the X, Y and Z axes so that the respective bridge outputs of the X, Y and Z axes are respectively measured by a digital voltage meter. A low voltage power supply of +5 V is utilized as the power supply for the sensor. Here, values from which the offsets of the respective axial outputs have been arithmetically decreased are plotted as the respective measurement points shown in FIG. 6.

Figure 7:
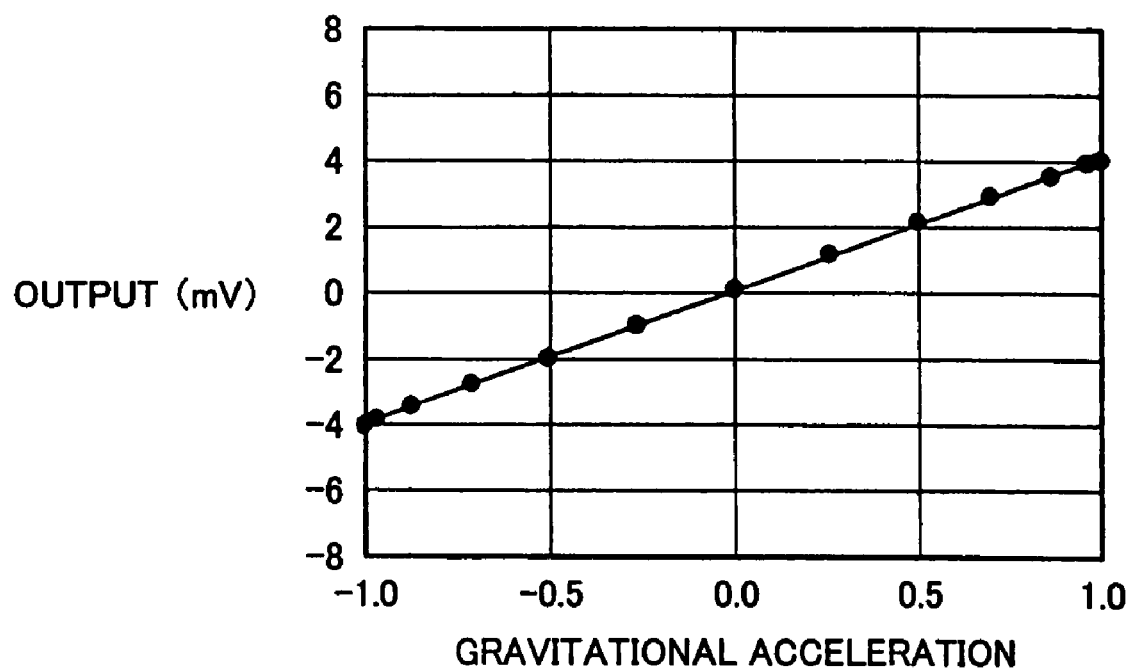
FIG. 7 is a graph for illustrating the relationship between the gravity acceleration (input) and output of sensor.

FIG. 7 is a graph for illustrating the relationship between the gravity acceleration (input) and output of sensor.

The input/output relationship shown in FIG. 7 is gained by calculating the gravity acceleration components which respectively relate to the X, Y and Z axes form the cosines of the inclination angles of FIG. 6 so as to find the relationship between the gravity acceleration (input) and the output of the sensor, and by evaluating the linearity of this input/output. That is, the relationship between the acceleration and the output voltage is approximately linear.

Figure 8:
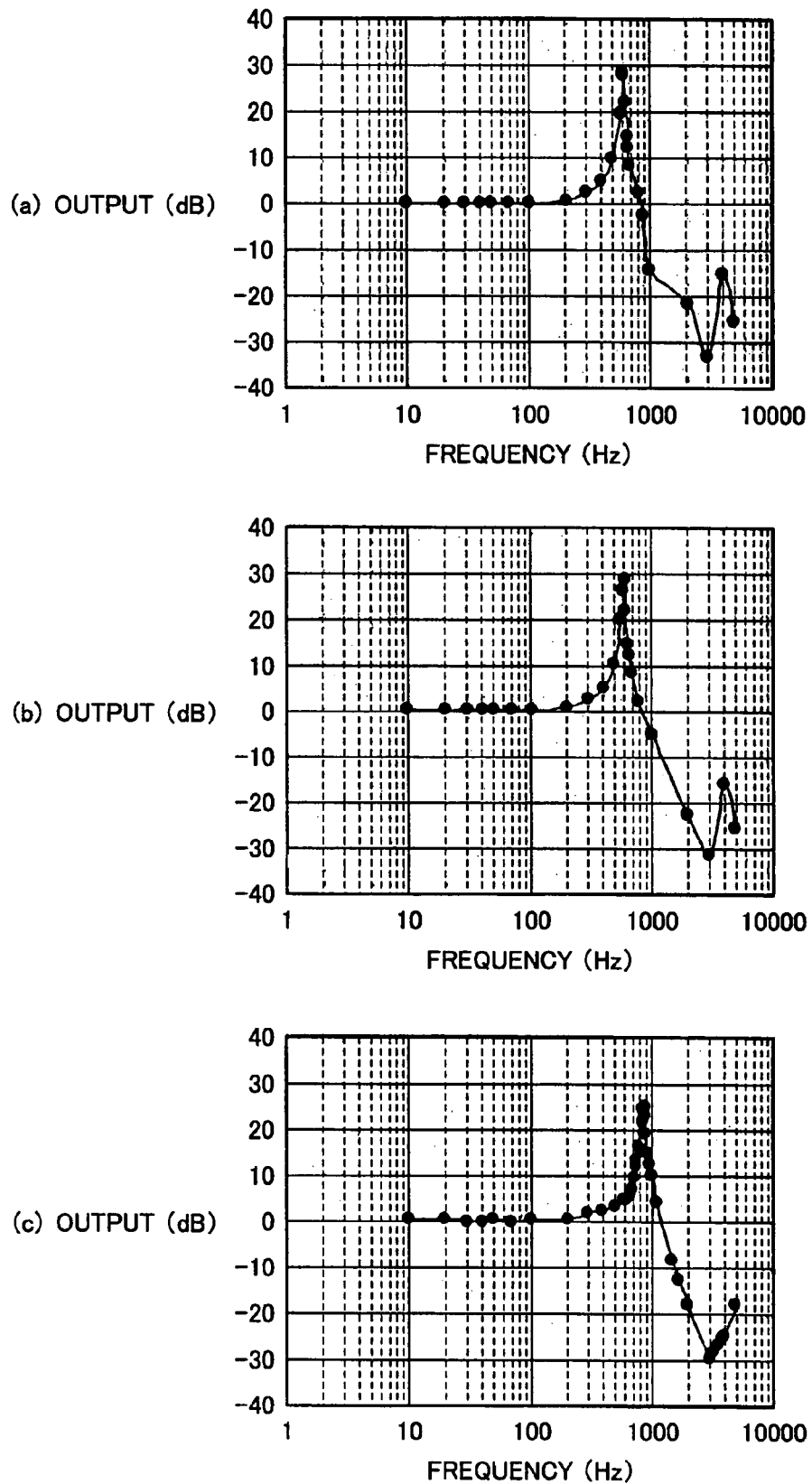
FIG. 8 is graphs for illustrating frequency properties of a three-axis acceleration sensor.

FIG. 8 is graphs for illustrating frequency properties of a three-axis acceleration sensor.

As shown in FIG. 8, the frequency properties of the outputs of sensors along the X, Y and Z axes, respectively, are indicated as flat frequency properties up to the vicinity of 200 Hz along all of the three axes, in an example where there are resonations at 602 Hz along the X axis, at 600 Hz along the Y axis and at 883 Hz along the Z axis.

With reference to FIG. 1 again, a method for inspecting a microstructure according to the embodiment of the present invention provides a system for outputting sound wave which is compression wave to a three-axis acceleration sensor that is a microstructure, and thereby, detecting the movement of the movable part of the microstructure on the basis of these sound wave, so as to evaluate the property thereof.

Figure 9:
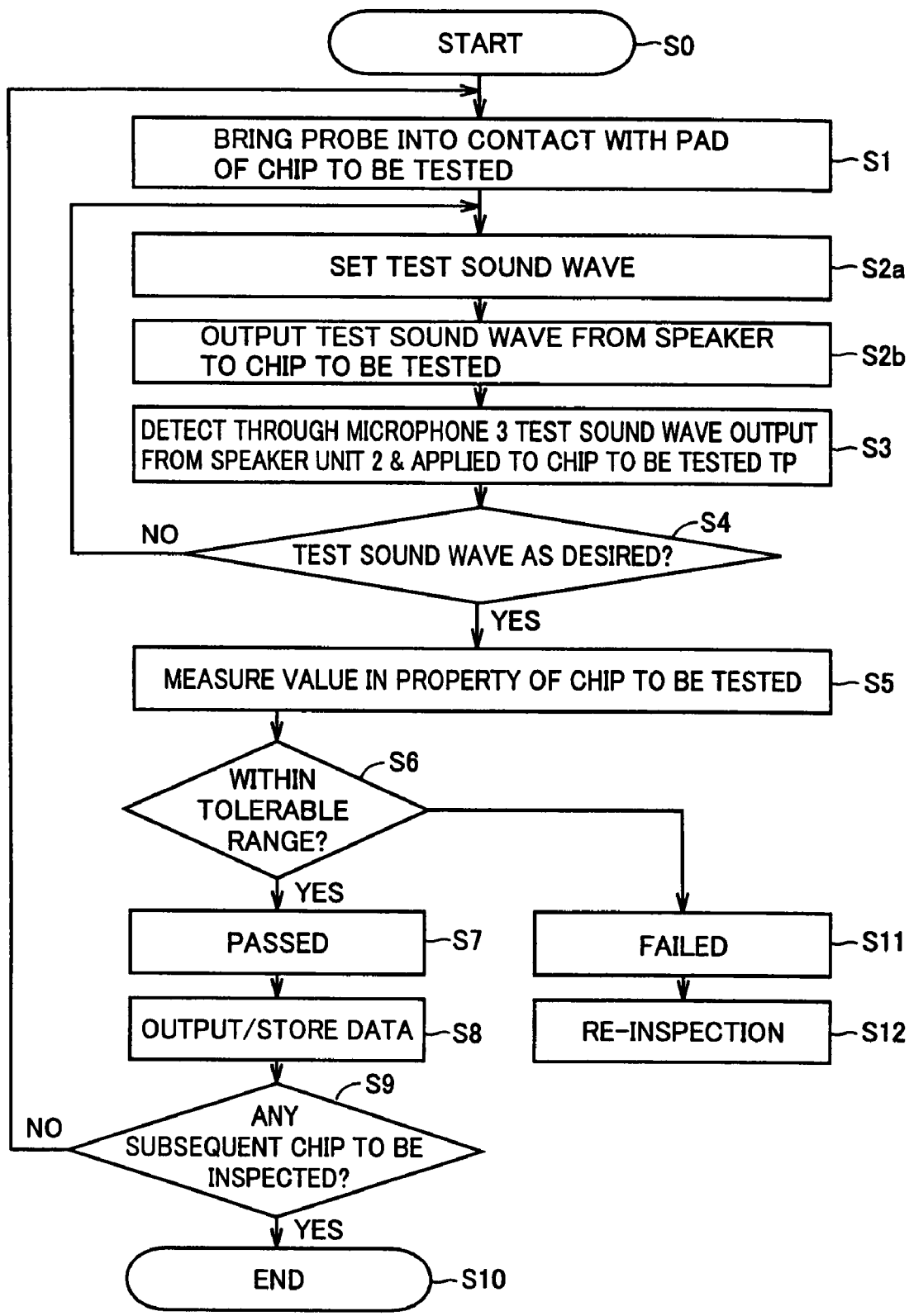
FIG. 9 is a flowchart for illustrating a method for inspecting a microstructure according to the first embodiment of the present invention.

With reference to the flowchart of FIG. 9, a method for inspecting a microstructure according to the first embodiment of the present invention is described. Note that herein for the sake of simplicity an example will initially be described such that a test sound wave is output from speaker unit 2 by a single sound source or speaker for the sake of illustration.

With reference to FIG. 9, first, inspection (testing) of a microstructure is started (step S0). Next, probe needles 4 are made to make contact with pads PD of chip to be tested TP (step S1). Specifically speaking, probe needles 4 are made to make contact with predetermined pads PD in order to detect the output voltage of the Wheatstone's bridge circuit described in FIG. 5. Here, though FIG. 1 shows a configuration where a pair of probe needles 4 is used, it is possible to provide a configuration where a number of pairs of probe needles are used. Employing a plurality of pairs of probe needles allows output signals to be detected in parallel.

Next, test sound wave that is outputted from speaker unit 2 is set (step S2a). Specifically speaking, control unit 20 receives an input of input data from the outside via input/output interface 15. Then, control unit 20 controls speaker control unit 30 and instructs speaker control unit 30 so that test sound wave having a desired frequency and a desired sound pressure provided to chip to be tested TP is outputted from speaker unit 2 on the basis of the input data. Next, test sound wave is outputted from speaker unit 2 to chip to be tested TP (step S2b).

Next, microphone 3 is used to detect test sound wave which is supplied to chip to be tested TP from speaker unit 2 (step S3). The test sound wave that has been detected by microphone 3 is converted to a voltage signal which is then amplified in signal adjustment unit 35, and the resulting signal is outputted to control unit 20.

Next, control unit 20 analyzes and determines the voltage signal that is inputted from signal adjustment unit 35, and determines whether or not desired test sound wave has reached the control unit (step S4).

In the case where control unit 20 determines desired test sound wave in step S4, the procedure goes to the next step S5, where the property value of the chip to be tested is measured. Specifically speaking, the property value is measured in measurement unit 25 on the basis of an electrical signal that is transmitted via probe needles 4 (step S5).

Specifically speaking, the movable part of a microstructure of the chip to be tested moves due to the arrival of test sound wave which is compression wave outputted form speaker unit 2, that is, air vibrations. A change in the resistance value of the three-axis acceleration sensor which is the microstructure that changes on the basis of this movement is measured on the basis of the output voltage that is supplied via probe needles 4.

Meanwhile, in the case where the signal is determined not to be desired test sound wave in step S4, the procedure returns to step S2a again, and the test sound wave is reset. At this time, control unit 20 instructs speaker control unit 30 to correct the test sound wave. Speaker control unit 30 microscopically adjusts the frequency and/or the sound pressure so as to gain desired test sound wave in response to the instruction from control unit 20, and thus, controls the system so that the desired test sound wave is outputted from speaker unit 2. Here, though a system where test sound wave is detected and corrected to desired test sound wave is described in the present embodiment, it is possible to provide a configuration where a part for correcting test sound wave and a system for correcting test sound wave are not particularly provided in the cases desired test sound wave reaches the microstructure of the chip to be tested in advance. Specifically speaking, processing up to steps S2a to S4 is implemented in advance before the start of testing, and a corrected control value for outputting desired test sound wave is stored in speaker control unit 30. Then, at the time of testing of the actual microstructure, speaker control unit 30 controls the input to speaker unit 2 with this recorded control value, and thereby, it becomes possible to omit the above-described processing in steps S3 and S4 at the time of testing.

Next, control unit 20 determines whether or not the measured property value, that is, measured data, is in an allowable range (step S6). In the case where it is determined to be in the allowable range in step S6, it is passed (step S7), and the outputting and storing of data are implemented (step S8). Then, the procedure goes to step S9. As an example of determination in the allowable range, in control unit 20, it is determined whether or not a desired output voltage is gained in response to the sound pressure of test sound wave which is outputted from speaker unit 2, or more concretely, whether or not the resistance value of the three-axis acceleration sensor changes in linear form in response to a change in the sound pressure of the test sound wave which is outputted from speaker, that is, whether or not the linear relationship described in FIG. 7 is gained, and thereby, whether or not the chip has appropriate property, can be determined. Here, data is stored in a storage unit, such as a memory, not shown, that is provided inside tester 5 on the basis of an instruction from control unit 20.

In the case where there is no chip to be inspected next in step S9, the inspection (testing) of a microstructure is completed (step S10).

Meanwhile, in the case where a chip to be inspected next exists in step S9, the procedure returns to the initial step S1, and the above-described inspection is again implemented.

Here, in the case where control unit 20 determines that the measured property value, that is, the measured data, is not in the allowable range in step S6, it is failed (step S11) and re-inspection is carried out (step S12). Specifically speaking, a chip that is determined to be outside of the allowable range can be removed through re-inspection. Alternatively, chips that are determined to be outside of the allowable range can be divided into a number of groups. That is, it is considered that many chips exist which are chips that cannot pass strict test conditions but do not cause any problems even if they are shipped after modification and correction. Accordingly, it is possible to select chips by grouping the chips through re-inspection and the like, and to ship some of the chips on the basis of the selection result.

Here, though in the present embodiment, a configuration is described as an example where a change in the resistance value of a piezoresistive element that is provided in a three-axis acceleration sensor is detected and determined by means of an output voltage in response to the movement of the three-axis acceleration sensor, it is also possible to provide a configuration where a change in the impedance value, such as that of a capacitor element or a reactance element, without being particularly limited to a resistor element, or a change in the voltage, the current, the frequency, the phase difference, the delay time and the position on the basis of a change in the impedance value is detected and determined.

Figure 10:
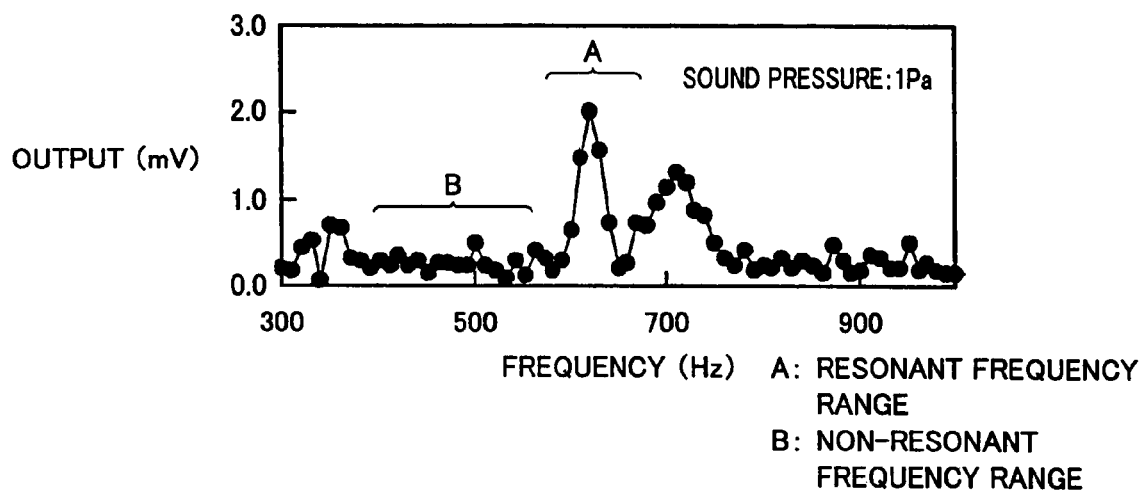
FIG. 10 is a graph for illustrating the frequency response of a three-axis acceleration sensor that responds to a test sound wave that has been outputted from a speaker unit 2.

FIG. 10 is a graph for illustrating the frequency response of a three-axis acceleration sensor that responds to test sound wave that has been outputted from a speaker unit 2.

FIG. 10 shows the output voltage that is outputted from a three-axis acceleration sensor in the case where test sound wave of 1 Pa (Pascal) is supplied as sound pressure, and the frequency thereof is changed. The vertical axis indicates the output voltage (mV) of the three-axis acceleration sensor, and the horizontal axis indicates the frequency (Hz) of the test sound wave.

Here, the output voltage that is gained in the direction of the X axis is particularly shown.

FIG. 10 shows two regions A and B. Specifically speaking, FIG. 10 shows resonant frequency region A, and non resonant frequency region B.

With reference to FIG. 10, the frequency where the output voltage is the maximum, that is, where the maximum output voltage that has changed as a result of resonation is gained corresponds to the resonant frequency. In FIG. 10, the frequency that corresponds to this output is approximately 600 Hz. That is, it almost coincides with the frequency property of the three-axis acceleration sensor along the X axis.

Accordingly, it is possible to specify the resonant frequency from the property of the output voltage that is gained when, for example, the frequency of test sound wave is changed while making the sound pressure constant, and it becomes possible to determine whether or not this specified resonant frequency is a desired resonant frequency after the comparison between this specified frequency and the desired resonant frequency. Though only the X axis is illustrated in the present embodiment, it is possible to gain the frequency properties along the X axis and the Z axis in the same manner, and therefore, the properties of the acceleration sensor along the three respective axes can be evaluated simultaneously.

In the case where, for example, resonation occurs in a frequency other than 600 Hz that is not the resonant frequency, an appropriate and desired frequency cannot be gained along this axis, and therefore, it is possible to determine that the system is defective. That is, it is difficult to conduct inspection from the appearance, particularly because this is a microstructure, while damage in the internal structure and a crack or the like that has occurred in the movable part of the microstructure can be inspected in the above-described manner. Here, though a case where the resonant frequency is specified from the maximum output voltage is described, the movable part has the maximum amount of displacement as a result of resonation. Accordingly, the frequency where the maximum amount of displacement is gained corresponds to the resonant frequency. As a result of this, the resonant frequency is specified from the maximum amount of displacement, and it is possible to determine whether or not a desired resonant frequency has been gained in the same manner as described above, so as to see if there are defects.

In addition, it is also possible to change the sound pressure of test sound wave using, for example, the frequency region of region B, that is, the non resonant frequency region, so as to perform detection and inspection of the sensitivity and the offset of a three-axis acceleration sensor from the output result.

Furthermore, though a system for inspecting one chip TP via probe needles 4 is described in the present embodiment, test sound wave spreads uniformly, and therefore, it is also possible to perform the same inspection on a number of chips in parallel. In addition, it is relatively easy to control the frequency and sound pressure of test sound wave, and therefore, the configuration of the unit can be made to be simple and easy, in comparison with the configuration of the unit for controlling the amount of flow of air.

As described above, the property of a microstructure can be inspected with high precision from the movement of the movable part of the microstructure in the configuration of an inspection method and an inspection device according to the first embodiment, which is a simple system for controlling sound wave which is compression wave.

While for the above described system an inspection method that employs a test sound wave of a single sound source has been described for the sake of simplicity, the present system is directed to a system employing a composite wave of a plurality of sound sources as a test sound wave applied to a movable part of a microstructure, and an inspection method is performed, similarly as done when a single sound source is employed. When a plurality of sound sources are employed, a test sound wave is generated, as will more specifically be described hereinafter.

Figure 11:
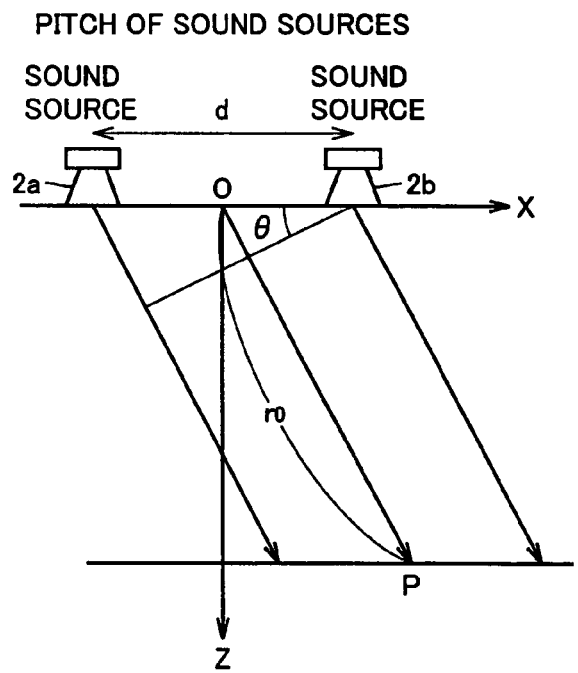
FIG. 11 is a diagram for illustrating a system generating a directional test sound wave in a microstructure inspection system in an embodiment of the present invention.

FIG. 11 is a diagram for illustrating a system generating a directional test sound wave in a microstructure inspection system in an embodiment of the present invention.

Herein, as shown in FIG. 11, speaker unit 2 is shown as two speakers 2a and 2b arranged along the X axis and having a pitch d. Hereinafter will be considered a test sound wave applied to a point P when it is radiated along the Z axis from a position O intermediate between speakers 2a and 2b. Between center position O and point P there is a distance r0 having a sufficiently larger value than pitch d for the sake of illustration. Herein, θ represents an angle formed between a vector of a test sound wave or a composite wave of sound waves output from speakers 2a and 2b, respectively, toward point P and the Z axis.

From the sound sources or speakers 2a and 2b to point P there are distances as represented by the following expressions:

$r0-(d/2) \sin θ$ (distance from speaker 2a to point P)
and $r0+(d/2) \sin θ$ (distance from speaker 2b to point P).

Thus there is a difference in distance by $d \sin θ$.

The speed potentials of point P by the sound sources or speakers 2a and 2b have a phase difference of $2π \, d\sin θ/λ$.

For example, d=20 mm, a sound wavelength λ=17 mm (frequency: 20 kHz), and from a sound source to an object to be measured there is distance r0=500 mm for the sake of illustration. By way of example, a sonic speed of 340 m/sec is adopted.

While $d \sin θ$ is sufficiently small in comparison with r0, $d \sin θ$ does not necessarily have a small value in comparison with wavelength λ.

Accordingly the two sound sources provide a composite sound field of 0 for a direction θ allowing $d \sin θ$ to be an odd multiple of λ/2, since their effects cancel each other. In contrast, they provide a maximized composite sound field for a direction allowing $d \sin θ$ to be an integer multiple of λ.

More specifically, when d>λ/2, a direction allowing a sound pressure of a maximum and a direction allowing a sound pressure of 0 will appear alternately. More specifically, the speed potential is represented by the following equation:

$$Φ=(Q/2π)\{\exp(-jkr0)/r0\}\cos[(kd/2)\sin θ],$$

wherein
Q: volume velocity $k=ω/c$ $ω=2πf$ $c=\sqrt{K/ρ}$

K: bulk modulus of medium
ρ: density of medium
c: sonic speed.

For θ=0, $$\Phi_0 = (Q/2\pi)\exp(-jkr0)/r0.$$

If directivity coefficient R (θ) is represented by $\Phi/\Phi_0$, then
If the speed potential is $$\Phi = \frac{Q}{4\pi r}e^{-jkr}$$

and from each sound source to the point to be measured there is a distance $r_i = r_0 + id\sin\theta$, then $$\Phi = \sum_{i=0}^{N-1}\frac{Q}{4\pi r_i}e^{-jkr_i} = \sum_{i=0}^{N-1}\frac{Q}{4\pi(r_0 + id\sin\theta)}e^{-jk(r_0+id\sin\theta)} =$$

$$\sum_{i=0}^{N-1}\frac{Q}{4\pi r_0(1+i(d/r_0)\sin\theta)}e^{-jk(r_0+id\sin\theta)},$$

where $r_0 \gg d$, so $$\Phi = e^{-jkr_0}\frac{Q}{4\pi r_0}\sum_{i=0}^{N-1}e^{-jkid\sin\theta}.$$

Herein, $$\sum_{i=0}^{N-1}e^{-jkid\sin\theta}$$

is a sum of a geometric expression with a first term of 1 and a geometric ratio $e^{-jkd\sin\theta}$, and if $e^{-jkd\sin\theta}$ is not 1, $$\Phi = e^{-jkr_0}\frac{Q}{4\pi r_0}\frac{e^{-jkNd\sin\theta}-1}{e^{-jkd\sin\theta}-1}.$$

If $$k = \frac{\omega}{c} = 2\pi f/c = 2\pi/\lambda$$

is substituted, $$\left(\Phi = e^{-jkr_0}\frac{Q}{4\pi r_0}\frac{e^{-2j\pi N(d/\lambda)\sin\theta}-1}{e^{-2j\pi(d/\lambda)\sin\theta}-1} = e^{-jkr_0}\frac{Q}{4\pi r_0}\frac{e^{-j\pi(2N-1)(d/\lambda)\sin\theta}-e^{j\pi(d/\lambda)\sin\theta}}{e^{-j\pi(d/\lambda)\sin\theta}-e^{j\pi(d/\lambda)\sin\theta}}\right)$$

$$\left(\left(\Phi = e^{-jkr_0}\frac{(Q)}{(4\pi r_0)}\frac{(e^{-j\pi(2N-1)(d/\lambda)\sin\theta}-e^{j\pi(d/\lambda)\sin\theta})}{(e^{-j\pi(d/\lambda)\sin\theta}-e^{j\pi(d/\lambda)\sin\theta})} = e^{-jkr_0}\frac{(Q)}{(4\pi r_0)}\frac{(e^{-j\pi N(d/\lambda)\sin\theta}-e^{j\pi N(d/\lambda)\sin\theta})}{(e^{-j\pi(d/\lambda)\sin\theta}-e^{j\pi(d/\lambda)\sin\theta})}e^{-j\pi(N-1)(d/\lambda)\sin\theta}\right)\right.$$

$$\left.\left(= e^{-jkr_0}\frac{(Q)}{(4\pi r_0)}\frac{\left(\frac{e^{-j\pi N(d/\lambda)\sin\theta}-e^{j\pi N(d/\lambda)\sin\theta}}{(2j)}\right)}{\left(\frac{e^{-j\pi(d/\lambda)\sin\theta}-e^{j\pi(d/\lambda)\sin\theta}}{(2j)}\right)}e^{-j\pi(N-1)(d/\lambda)\sin\theta}\right)\right)$$

Therefore $$\Phi = e^{-jkr_0}\frac{Q}{4\pi r_0}\frac{\sin[\pi N(d/\lambda)\sin\theta]}{\sin[\pi(d/\lambda)\sin\theta]}e^{-j\pi(N-1)(d/\lambda)\sin\theta}.$$

If a speed potential for θ=0 is $\Phi_0$, and $$\Phi = e^{-jkr_0}\frac{Q}{4\pi r_0}\sum_{i=0}^{N-1}e^{-jkid\sin\theta}$$

is used to obtain $\Phi_0$, then for θ=0, $e^{-jkd\sin\theta}=1$, and $$0 = 0,\ e^{-jkd\sin\theta} = 1,\ \text{and}\ \sum_{i=0}^{N-1}e^{-jkid\sin\theta} = N.$$

Therefore, $$\Phi_0 = e^{-jkr_0}\frac{QN}{4\pi r_0}.$$

If directivity coefficient $$R(\theta) = \frac{\Phi}{\Phi_0},$$

$$R(\theta) = \frac{\Phi}{\Phi_0} = \left|\frac{\sin[\pi N(d/\lambda)\sin\theta]}{N\sin[\pi(d/\lambda)\sin\theta]}\right|\left|e^{-j\pi(N-1)(d/\lambda)\sin\theta}\right| = \left|\frac{\sin[\pi N(d/\lambda)\sin\theta]}{N\sin[\pi(d/\lambda)\sin\theta]}\right|,$$

where $|e^{-j\pi(N-1)(d/\lambda)\sin\theta}|=1$.

Therefore, $$R(\theta) = |\cos(X)| = \left|\frac{\sin[\pi N(d/\lambda)\sin\theta]}{N\sin[\pi(s/\lambda)\sin\theta]}\right|.$$

$R(\theta)=|\cos(X)|=|\sin(\pi N(d/\lambda)\sin\theta)/N\sin(\pi(d/\lambda)\sin\theta)|$.

Figure 12:
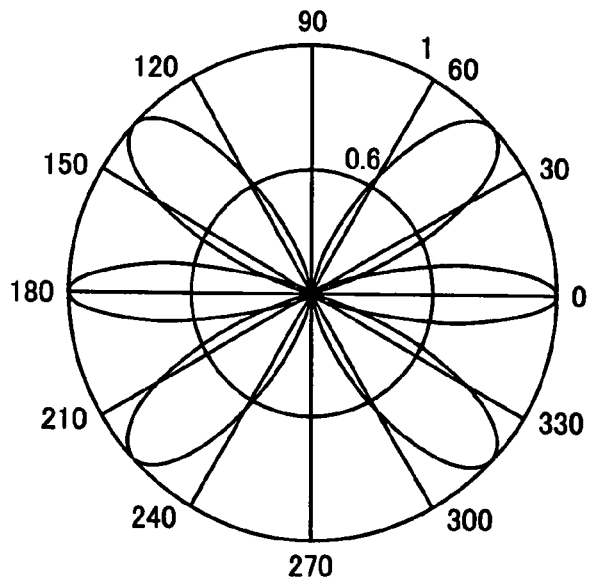
FIG. 12 is a diagram for illustrating R (θ) for d/λ=1.5

Note that FIG. 12 is a diagram for illustrating R (θ) for d/λ=1.5, wherein d=25.5 mm and λ=17 mm for the sake of illustration.

Figure 13:
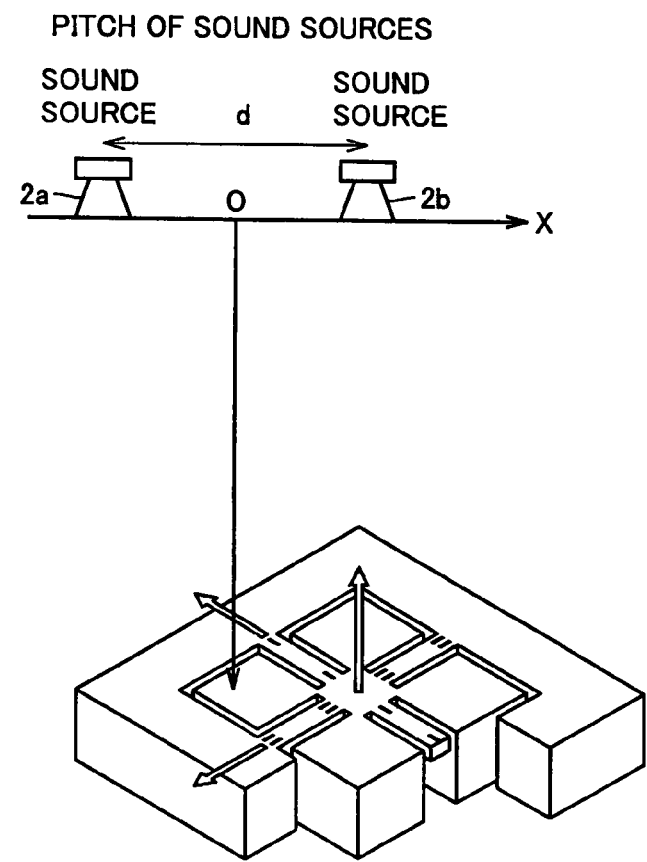
FIG. 13 is a diagram for illustrating a test sound wave applied only to a predetermined movable part.

Accordingly, if a movable part of a microstructure to be measured is placed at a location allowing R (θ)=1 a composite test sound wave can be applied only to a particular, predetermined movable part, as shown in FIG. 13. This example shows a test sound wave applied to a three-axis acceleration sensor only at one proof mass.

Figure 14:
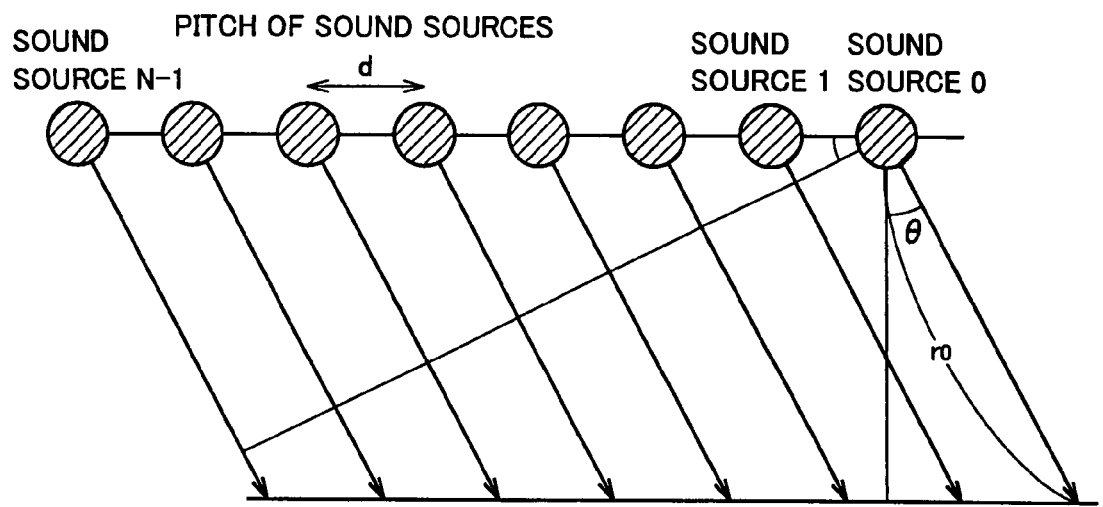
FIG. 14 is a diagram for illustrating a sound field to which a test sound wave is applied when a plurality of sound sources are arranged along the X axis.

FIG. 14 is a diagram for illustrating a sound field to which a composite wave generated by a plurality of sound sources arranged along the X axis is applied as a test sound wave.

As shown in FIG. 14, N sound sources are shown. Furthermore, r0>>d for the sake of illustration. Adjacent sound sources have a difference dsin θ in the distance to a point to be measured, as aforementioned.

The speed potential is represented by the following expression:

For θ=0, R (θ)=1, and only in this direction the sound wave is intensely radiated. If there is an angle other than θ=0 that satisfies (d/λ) sin θ=1, (sin θ=λ/d), the sound wave is also intensely radiated in that direction.

Figure 15:
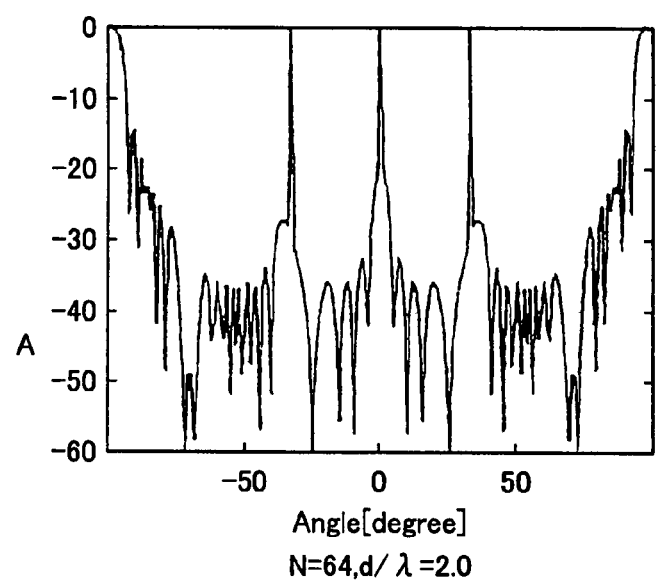
FIG. 15 is a graph for illustrating a relationship between an angle at which each sound source outputs a sound wave and sound pressure.

FIG. 15 is a graph for illustrating a relationship between an angle at which each sound source outputs a sound wave and sound pressure.

In this example N=64 and d/λ=2. In this case if there is an angle other than θ=0 that satisfies (d/λ) sin θ=1, i.e., d/λ=sin θ, the sound wave is intensely radiated only in that direction.

Figure 16:
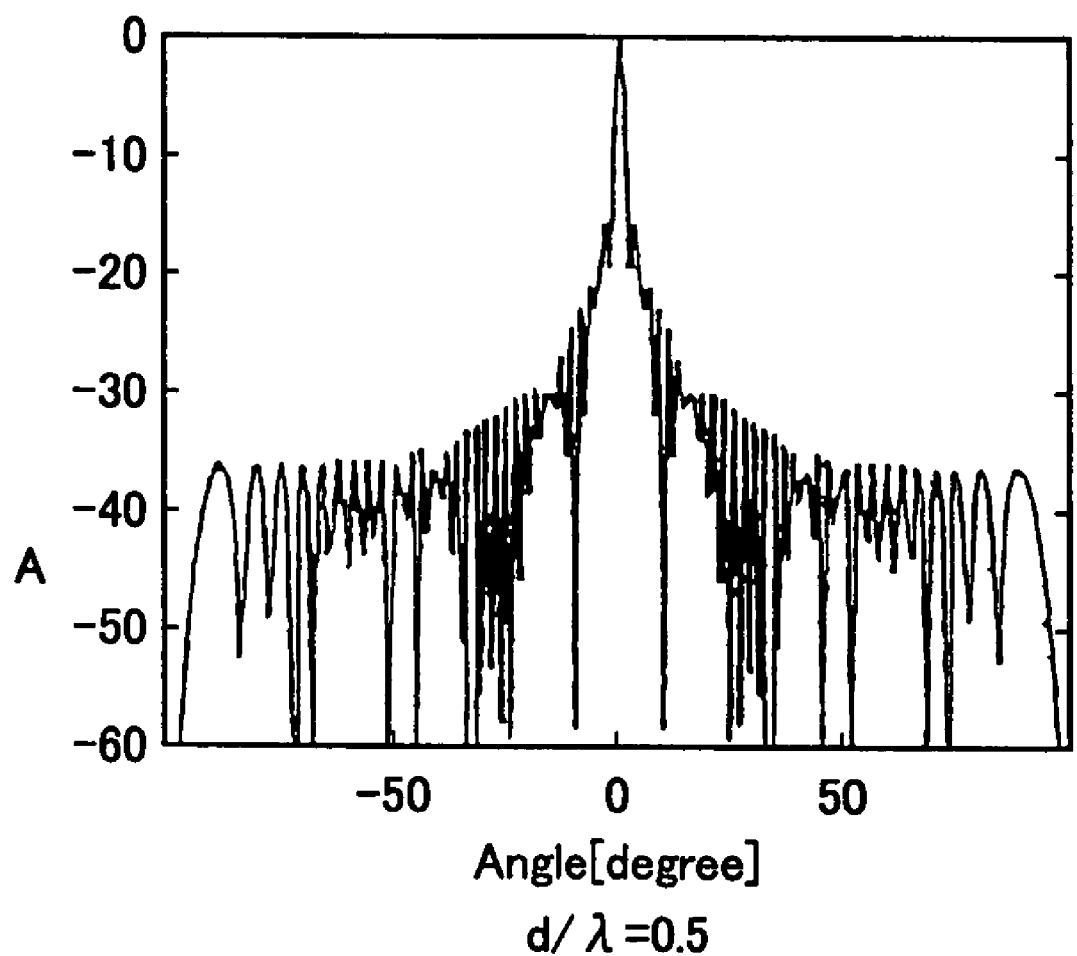
FIG. 16 is another graph for illustrating a relationship between an angle at which each sound source outputs a sound wave and sound pressure.

FIG. 16 is another graph for illustrating a relationship between an angle at which each sound source outputs a sound wave and sound pressure. This is a case for d/λ=0.5. In this case the sound wave is intensely radiated only in a direction of θ=0.

Thus, from the above relationship, the sound sources can be spaced by a distance having a prescribed value set as based on their difference in the distance to the movable part of the microstructure and a sound wave's wavelength to provide adjustment to maximize a composite sound field of a test sound wave applied to the movable part of the microstructure in the form of a composite wave. More specifically, appropriately setting a parameter of the above relationship can provide adjustment to maximize a composite sound field of test sound waves. For example, if the sound sources have a difference in the distance to the movable part of the microstructure, as predefined, and are spaced as predefined, adjusting the sound waves in wavelength can provide adjustment to maximize a composite sound field of test sound waves at a prescribed position. This can be done for example by speaker control unit 30 providing an instruction to adjust a wavelength, more specifically a frequency of a sound wave of each sound source of speaker unit 2. Note that the speed potential, volume velocity, directivity coefficient and the like in the above relationship are described in detail in "Mechanical Acoustics", Kimihiko Yasuda, issued Jul. 16, 2004, Corona Publishing Co., Ltd., pp. 11-16 and 106-116.

Thus in the present embodiment a composite wave of sound waves output from a plurality of sound sources can be employed as a test sound wave and the test sound wave can be provided with directivity to provide a composite sound field maximized in sound pressure, and the test sound wave can thus be applied to an object to be measured, e.g., a proof mass of the acceleration sensor above described. This allows a simple system to be employed to efficiently and with high precision inspect a structure having a micro movable part.

Figure 17:
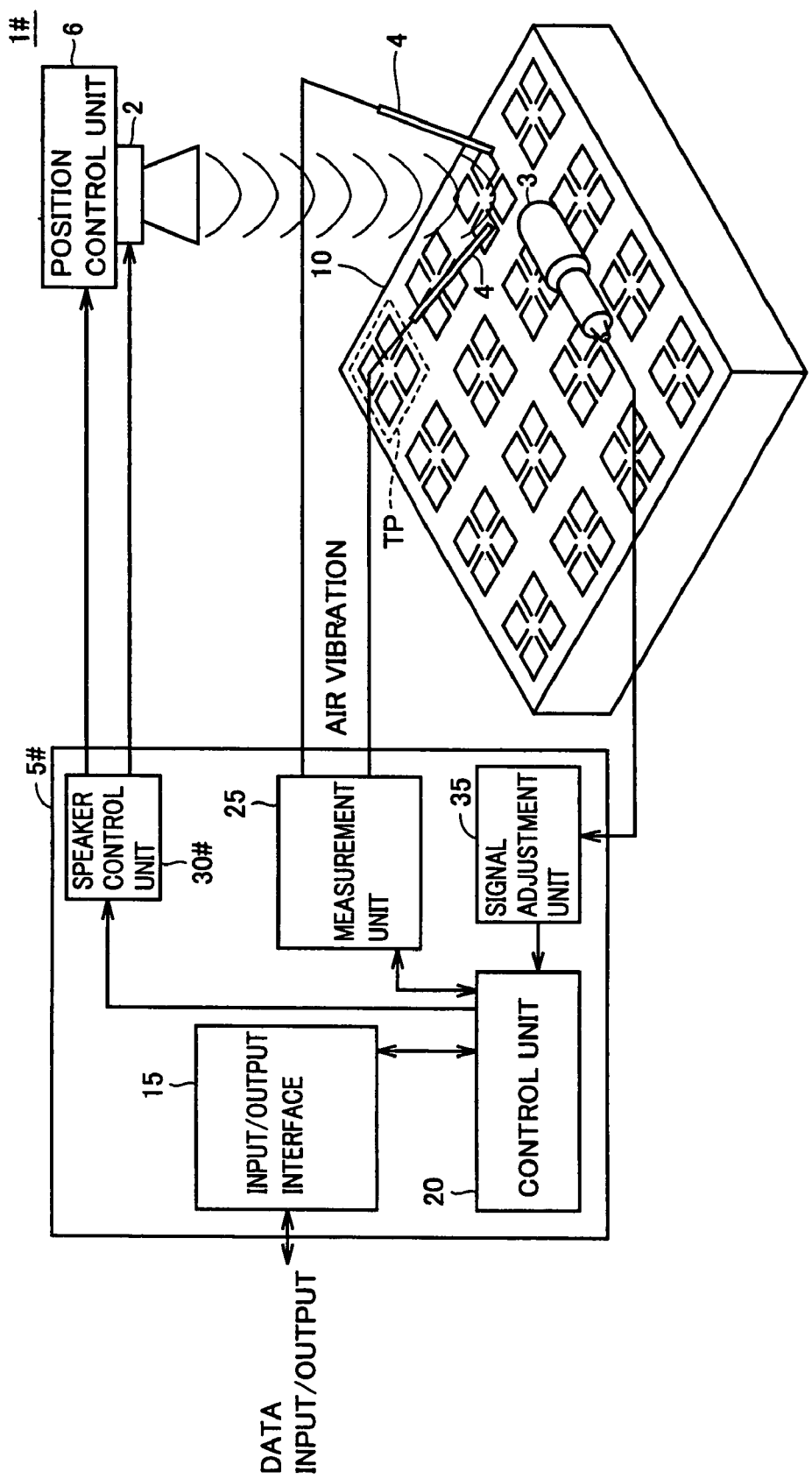
FIG. 17 schematically shows a configuration of another microstructure inspection system 1# in accordance with the first embodiment of the present invention.

FIG. 17 schematically shows a configuration of another microstructure inspection system 1# in accordance with the first embodiment of the present invention.

With reference to FIG. 17, the present invention in the first embodiment provides another inspection system 1# different in that tester 5 is replaced with a tester 5#. More specifically, tester 5# is similar to tester 5 except that speaker control unit 30 is replaced with a speaker control unit 30# and that and a position control unit 6 is additionally provided for speaker unit 2. The remainder is similarly provided and thus will not be described repeatedly.

Position control unit 6 is assumed to be controlled by speaker control unit 30# to positionally adjust speaker unit 2, more specifically, a speaker serving as each sound source configuring speaker unit 2, as desired. Speaker control unit 30# is assumed to be responsive to an instruction received from control unit 20 to output a signal to instruct position control unit 6 to move the speakers of speaker unit 2 to a desired position. For example, position control unit 6 may be implemented by a manipulator having a mechanism of mutually connected slides or in the form of an arm having a rotative joint allowing multiple degrees of freedom to positionally adjust the speaker or each sound source configuring speaker unit 2.

By this configuration, position control unit 6 can positionally adjust each sound source or speaker, as desired, i.e., control a site to which a maximized sound pressure is applied. A composite test sound wave can be applied to a microstructure at a desired position, and a structure having a micro movable part can thus be inspected efficiently with high precision. Note that while herein position control unit 6 is provided to positionally adjust speaker unit 2, it can of course be provided for example for a microphone 3 or the like, as well as speaker unit 2, to positionally control it. Furthermore, while the above configuration has been described for a system positionally adjusting a sound source, the sound source may be fixed and an object to be measured may instead be positionally adjusted, and a composite test sound wave may be applied to a desired position. Alternatively, a manipulator or the like may be positionally adjusted to apply a test sound wave to a desired position.

Second Embodiment

In the first embodiment, sound sources are spaced by an interval adjusted to provide a maximized composite sound field. In the second embodiment will be described a system, also referred to as a so-called beam focusing system, allowing sound waves output from a plurality of sound sources to concurrently arrive at a movable part.

Figure 18:
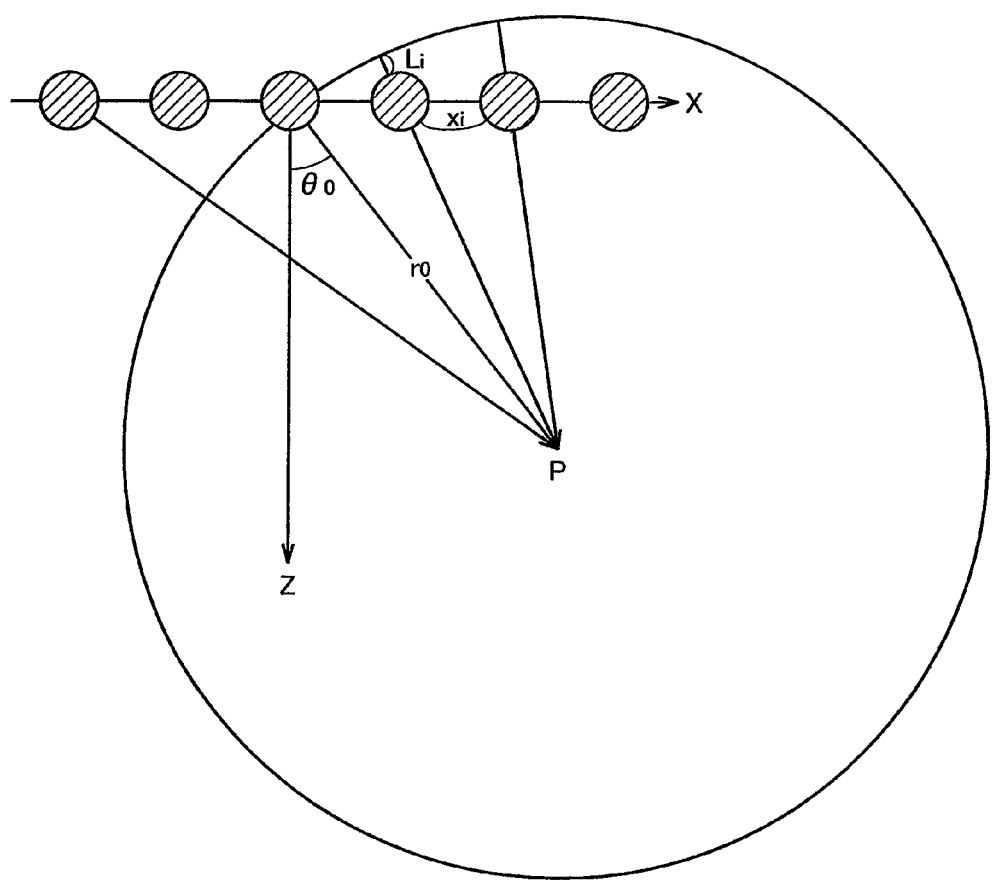
FIG. 18 illustrates that when a concentric circle having a radius r0 is drawn with a point P serving as its center, between the distance from each sound source to the observation point P and r0 there is a difference Li in distance.

FIG. 18 illustrates that when a concentric circle having a radius r0 is drawn with point P serving as its center, between the distance from each sound source to the observation point P and r0 there is a difference Li in distance.

This relationship is represented by the following equation:

$$Li = r0 - \sqrt{r0 \times r0 + Xi \times Xi - 2r0Xi\sin\theta_0},$$

where Xi represents a distance between the sound sources.

As shown in FIG. 18, focusing at a single, point P can be achieved by exerting control to drive each sound source at a time delayed by a time of τi=Li/c to output a sound wave so that the sound wave output from each sound source arrives at point P concurrently. Alternatively, each sound source can be controlled to provide a phase difference delayed by kLi. Note that c and k are represented as follows:

$$c = \sqrt{k/\rho}, \, k = \omega/c, \, \omega = 2\pi f.$$

Thus, as described in the second embodiment, sound waves can arrive at a prescribed point concurrently to provide a composite sound field maximized in sound pressure and thus apply a composite sound wave of the sound waves, or a test sound wave, to a proof mass. A simple system can be employed to efficiently and with high precision inspect a structure having a micro movable part.

Figure 19:
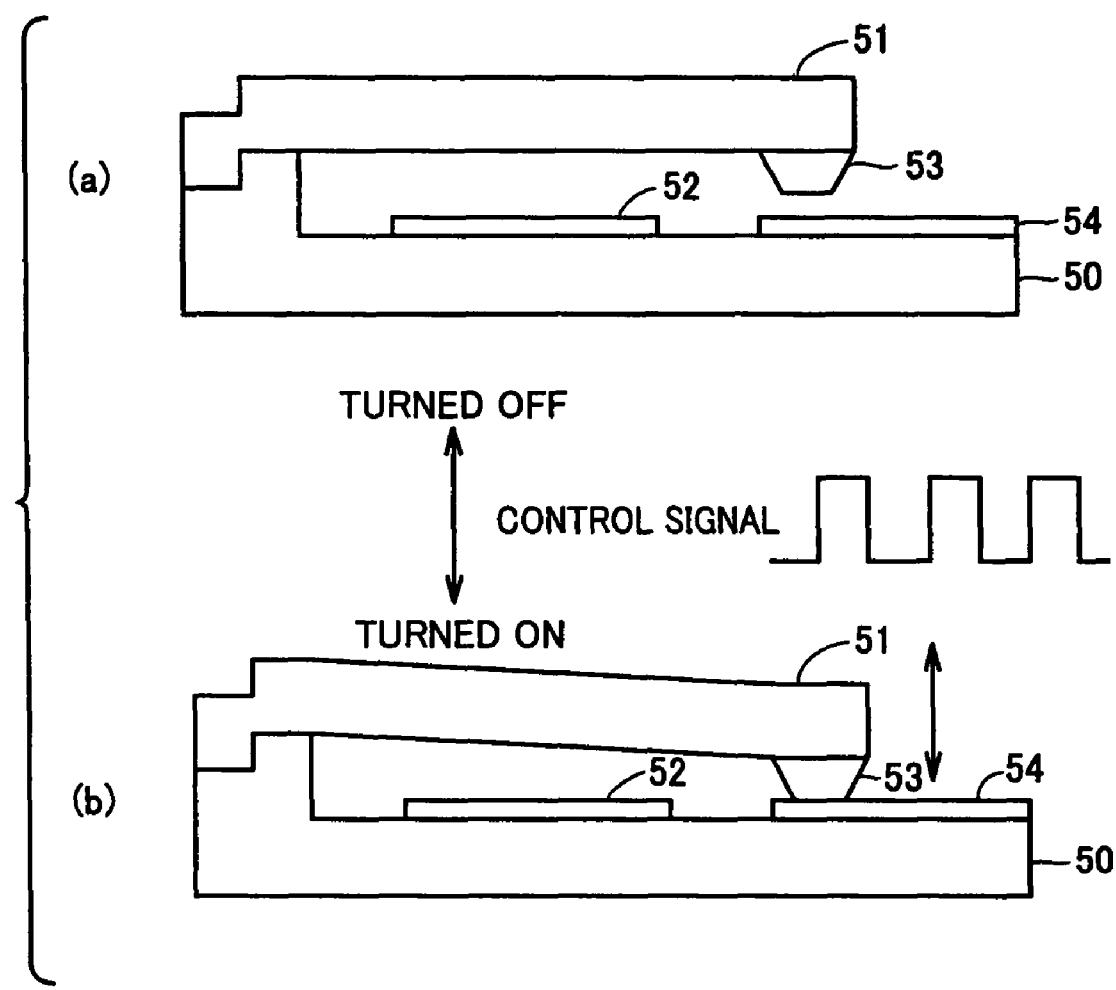
FIG. 19 is a conceptual diagram for schematically illustrating a cantilevered MEMS switch.

FIG. 19 is a conceptual diagram for schematically illustrating a cantilevered MEMS switch.

FIG. 19(a) is a diagram for illustrating a case where a switch is stationary. With reference to FIG. 19(a), the switch is formed of a substrate 50, a cantilever 51, a control electrode 52, a cantilever joining part 53 and a joining electrode 54. In the state where no control signal is inputted, the switch does not operate.

FIG. 19(b) is a diagram for illustrating a case where the switch operates. When a control signal is supplied to control electrode 52, cantilever 51 is attracted to the control electrode 52 side. As a result of this, cantilever joining part 53 makes contact with joining electrode 54. As a result of this, the switch becomes of the ON state. When a control signal in pulse form is supplied to control electrode 52, for example, cantilever joining part 53 moves upward and downward, repeating the joined state/non-joined state to joining electrode 54. This switch is microscopic, and is utilized as a switch for changing the frequency at high speed.

A composite test sound wave can be applied to an end portion of cantilever 51, or a movable part of the switch, in accordance with a system similar to that described above to inspect a property of the switch, similarly as done for the three-axis acceleration sensor.

FIG. 20 is a diagram for illustrating a case where an illumination window of an electron beam illuminator has a membrane structure. As shown in FIG. 20, electron beam EB is emitted into the air from a vacuum tube 81 through an illumination window 80, and an enlarged cross section of a portion of illumination window 80 shows that a membrane structure is adopted in the thin film. Here, though FIG. 20 illustrates only one membrane structure where the membrane is formed of a single material, in some cases, the membrane may be formed of a number of materials so as to have a multi-layered film structure, or may be formed as an illumination window where membrane structures are arranged in an array. When a composite test sound wave in accordance with a system similar to that described above is applied to a portion of such a structure of membrane of thin film as described above, the membrane of the thin film, or a movable part, vibrates. It is thus possible to inspect the presence/absence of damage or a crack in the film, or the film quality, and other properties.

Figure 21:
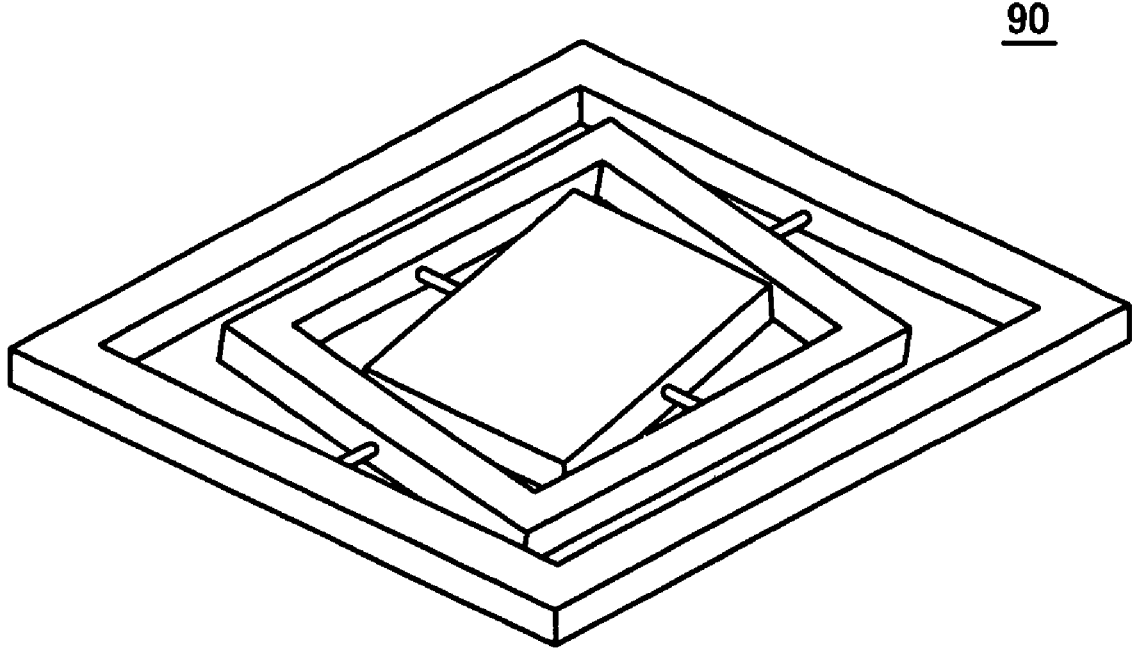
FIG. 21 is a diagram for illustrating a torsion mirror 90.

FIG. 21 is a diagram for illustrating a torsion mirror 90.

As shown in FIG. 21, it is configured of a rotative center portion, a rotative frame portion outer than the center portion, and a peripheral portion outer than the frame portion. The rotative center portion and the rotative frame portion can rotate about different axes of rotation, respectively.

Torsion mirror 90 can also be exposed at a specific, rotating portion serving as a movable part to a composite test sound wave in accordance with a system similar to that described above to rotate at least a portion of torsion mirror 90 about an axis of rotation to inspect a property thereof.

Thus the test sound wave in accordance with the first and second embodiments can be applied not only to a three-axis acceleration sensor, as described above, but also another MEMS having a movable part, as described above. A simple system can be employed to efficiently and with high precision inspect a structure having a micro movable part. Furthermore, the test sound wave in accordance with the first and second embodiments can also be applied not only to the three-axis acceleration sensor but also e.g., an angular rate sensor or a multi-axial angular rate sensor at a particular portion for example functioning as a movable part to achieve an effect similar to that achieved when the three-axis acceleration sensor is inspected.

Third Embodiment

The second embodiment has been described for a system positionally adjusting a plurality of sound sources in accordance with a mechanical system employing a manipulator or the like. In the third embodiment will be described a system capable of positionally adjusting a plurality of sound sources in accordance with a simple system.

Figure 22:
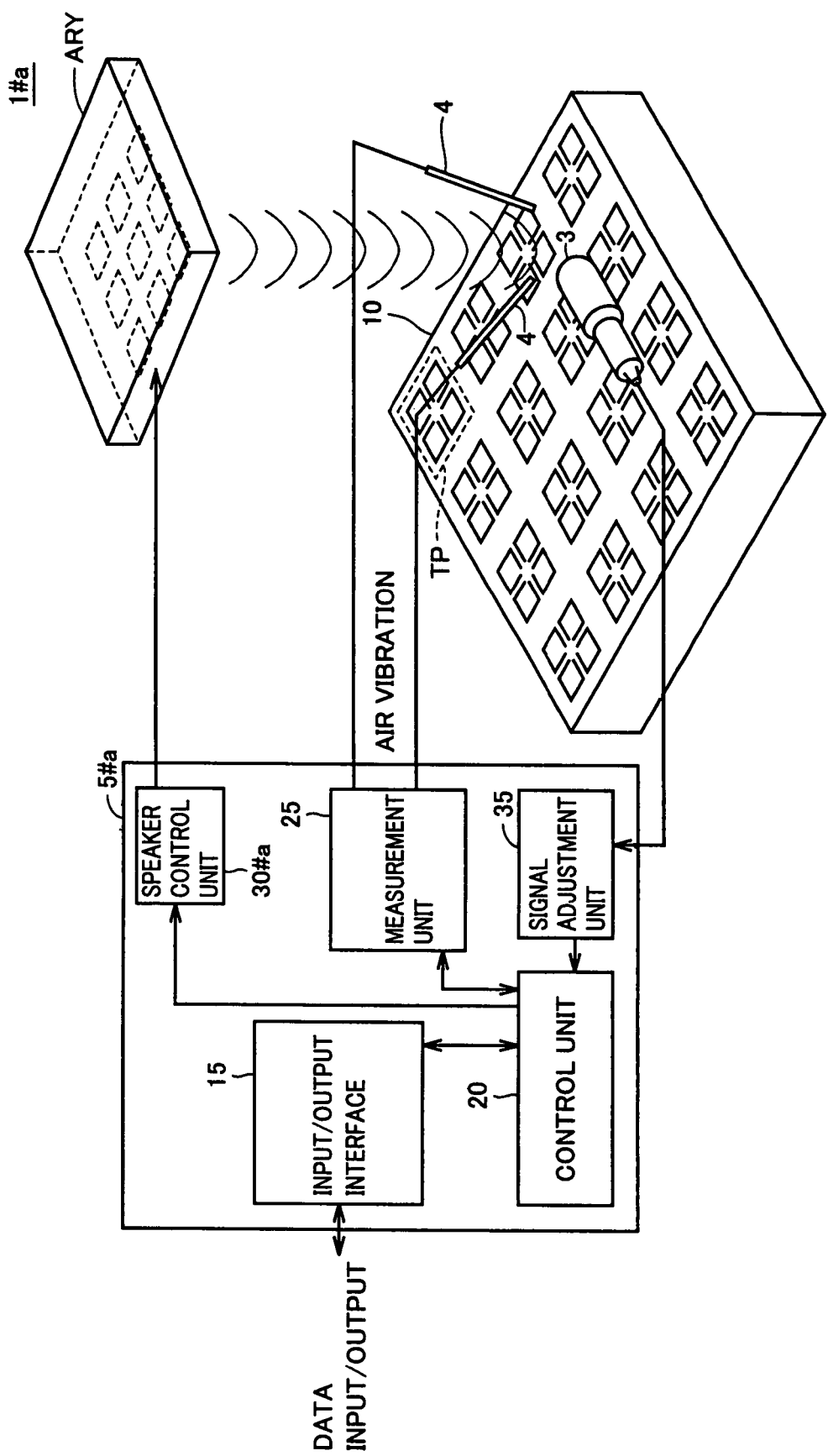
FIG. 22 schematically shows a configuration of a microstructure inspection system 1#a in accordance with a second embodiment of the present invention.

FIG. 22 schematically shows a configuration of a microstructure inspection system 1#a in accordance with the second embodiment of the present invention.

With reference to FIG. 22 the present invention in the second embodiment provides microstructure inspection system 1#a different in that tester 5 is replaced with a tester 5#a. More specifically, tester 5#a is different in that speaker unit 2 is replaced with a speaker unit ARY and that speaker control unit 30 is replaced with a speaker control unit 30#a. The remainder is similar and accordingly will not be described repeatedly.

Speaker control unit 30#a operates in response to an instruction received from control unit 20 to control speaker unit ARY, as will be described hereinafter more specifically.

Figure 23:
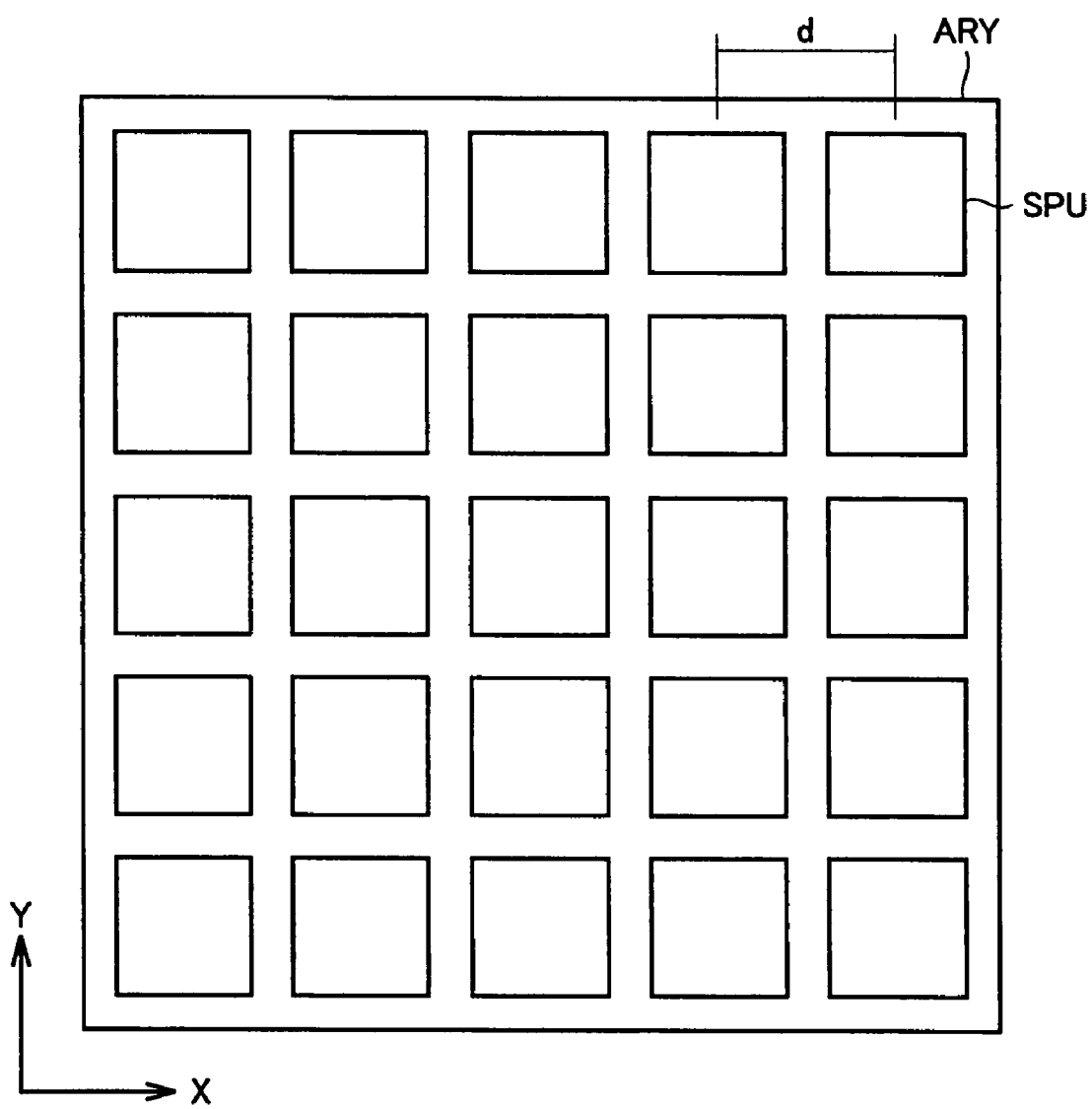
FIG. 23 is a diagram for generally illustrating a speaker unit ARY in accordance with a third embodiment of the present invention.

FIG. 23 is a diagram for generally illustrating speaker unit ARY in accordance with the third embodiment of the present invention.

With reference to FIG. 23, the present invention in the third embodiment provides speaker unit ARY including a plurality of sub speaker units SPUs arranged in a matrix, and a switch unit (not shown) for controlling sub speaker unit SPU to turn on/off. By way of example, sub speaker units SPUs have a pitch d for the sake of illustration.

Figure 24:
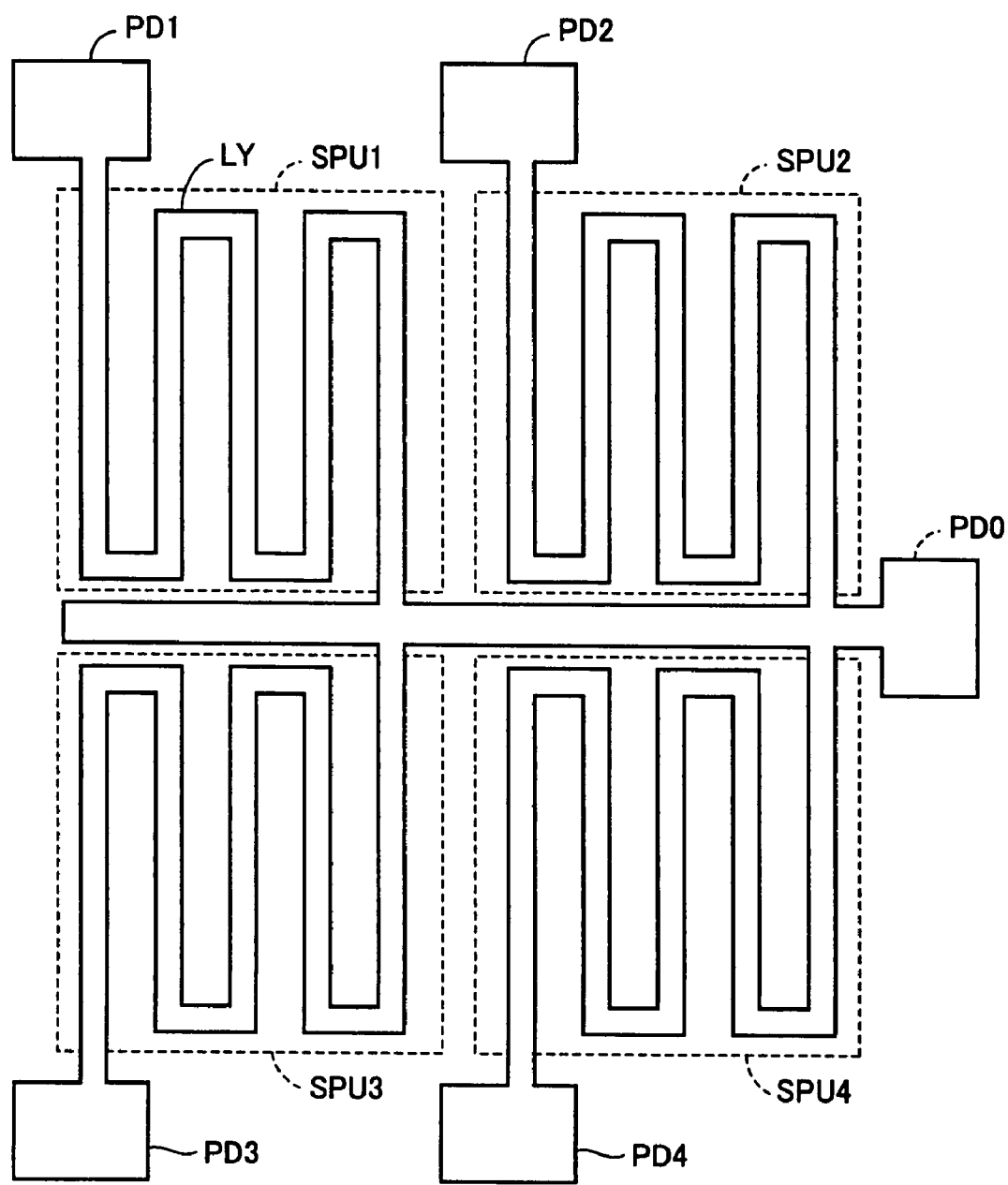
FIG. 24 is a diagram for illustrating a portion of speaker unit ARY.

FIG. 24 is a diagram for illustrating a portion of speaker unit ARY.

With reference to FIG. 24, herein, an interconnection on an upper surface of 2×2 sub speaker units is shown. Herein, by way of example, sub speaker units SPU1-SPU4 are shown.

Herein as one example of sub speaker unit SPU a thermoacoustic engine capable of providing a medium with heat to allow thermal induction to cause air to be compressional to generate a sound wave will be described.

Sub speaker unit SPU is configured as will now be described hereinafter.

Figure 25:
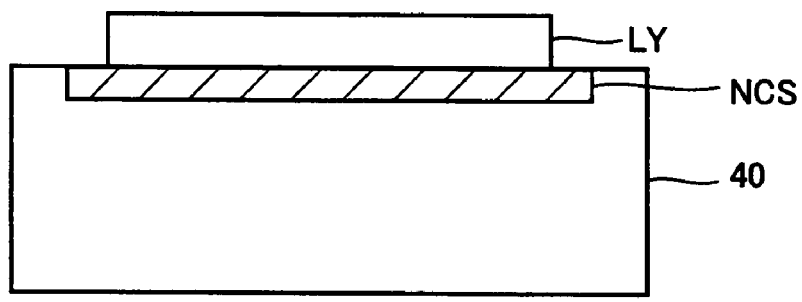
FIG. 25 shows a structure in cross section of a sub speaker unit SPU.

FIG. 25 shows a structure in cross section of sub speaker unit SPU.

With reference to FIG. 25, sub speaker unit SPU includes a semiconductor substrate 40 implemented by a monocrystalline silicon substrate, a thermal insulation layer NCS provided in one surface of semiconductor substrate 40, as seen depthwise, and reaching a predetermined width in semiconductor substrate 40, and a heating element LY provided in the form of a thin film of metal, e.g., Al, deposited on thermal insulation layer NCS. Thermal insulation layer LY is formed of a porous nanocrystalline silicon layer and sufficiently smaller in thermal conductivity and volumetric heat capacity than semiconductor substrate 40.

Although not shown, when an alternate-current power supply provides an alternate current to pass through heating element LY, heating element Ly generates heat, and varies in temperature (or generates heat in an amount varying) with the frequency of the alternate current passing therethrough. As heating element LY immediately overlies thermal insulation layer NCS and is thus thermally insulated from semiconductor substrate 40, heating element LY efficiently exchanges heat the air surrounding it, and as heating element LY varies in temperature or generates heat in the variable amount, the air repeats expansion and contraction and as a result a sound wave is generated.

Again, with reference to FIG. 24, the figure shows the thin metal film meandering immediately on the porous silicon layer to allow heating element LY to exchange heat more efficiently. Furthermore, for each sub speaker unit SPU, the heating element has one and the other ends provided with pads. For example, for sub speaker unit SPU1, heating element LY has one and the other ends provided with pads PD1 and PD0, respectively. The other sub speaker units SPU2 to SPU4 are also similarly configured. Pad PD0 are shared and electrically coupled with an alternate-current power supply to pass an alternate current through the heating element.

The monocrystalline silicon substrate serving as semiconductor substrate 40 has one surface provided with a porous nanocrystalline silicon layer serving as thermal insulation layer NCS, as described above, which is provided by anodization.

Figure 26:
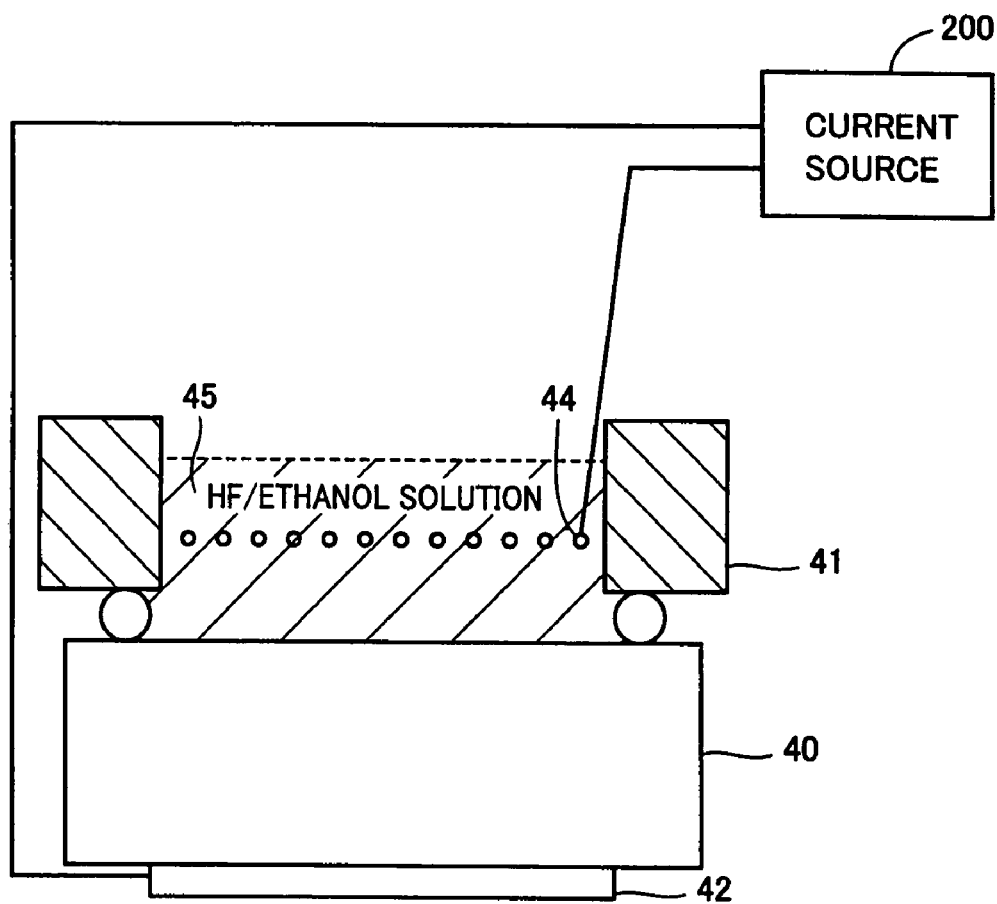
FIG. 26 is a diagram for illustrating how a thermal insulation layer NCS is prepared.

FIG. 26 is a diagram for illustrating how thermal insulation layer NCS is prepared.

With reference to FIG. 26, the anodization process is performed as follows: a seal is provided to form an external wall 41 surrounding a portion of a surface of semiconductor substrate 40 that is anodized, and inside the external wall an electrolyte 45 is introduced to expose the portion to electrolyte 45.

Subsequently in electrolyte 45 a platinum electrode 44 is placed opposite the surface of semiconductor substrate 40. Furthermore for electrical conduction an electrode 42 is attached on a back surface of semiconductor substrate 40, and a lead connected to electrode 42 is connected to a current source 200 at a positive terminal and platinum electrode 44 is connected to current supply 200 at a negative terminal. Electrode 42 serves as an anode and platinum electrode 44 serves as a cathode, and from current supply 200 a current of a prescribed current density is passed between electrode 42 and platinum electrode 44 for a predetermined period of time for electrical conduction.

Such an anodization process provides thermal insulation layer NCS deposited inside external wall 41 on a portion of a surface of semiconductor substrate 40 and substantially uniform in thickness. Furthermore in the anodization process electrolyte 45 is for example 55 wt % of an aqueous solution of hydrogen fluoride and ethanol mixed together at a ratio of 1:1 (an HF/ethanol solution). The seal can be formed for example of fluoroplastic.

This system thus allows thermal insulation layer NCS to be implemented by a porous nanocrystalline silicon layer.

Note that heating element LY can be provided by the following process: a thin metal film is sputtered or the like on a surface of semiconductor substrate 40. On the thin metal film, photoresist is applied. Photolithography is employed to provide a patterned resist layer. The resist layer is used as a mask to so-called dry-etch or wet-etch away an unnecessary portion of the thin metal film. Finally the resist layer is removed to provide heating element LY for example meandering as described with reference to FIG. 24.

The above described system allows a plurality of independent sound sources to be readily formed in a matrix as shown in FIG. 22. More specifically, a semiconductor process can be employed to form a plurality of sound sources on a single substrate collectively and inexpensively. Furthermore, this process can minimize a difference in property between the sound sources and their displacement in arrangement. This can minimize variation, error and the like of a composite sound field in generating a composite wave from the plurality of sound sources.

Note that sub speaker unit SPU or each sound source can be sized to be 3 mm or smaller. This ensures a large number of sound sources for speaker unit ARY at a time and can help to provide sound sources densely. This allows a composite wave to provide a composite sound field sufficient in intensity.

Figure 27:
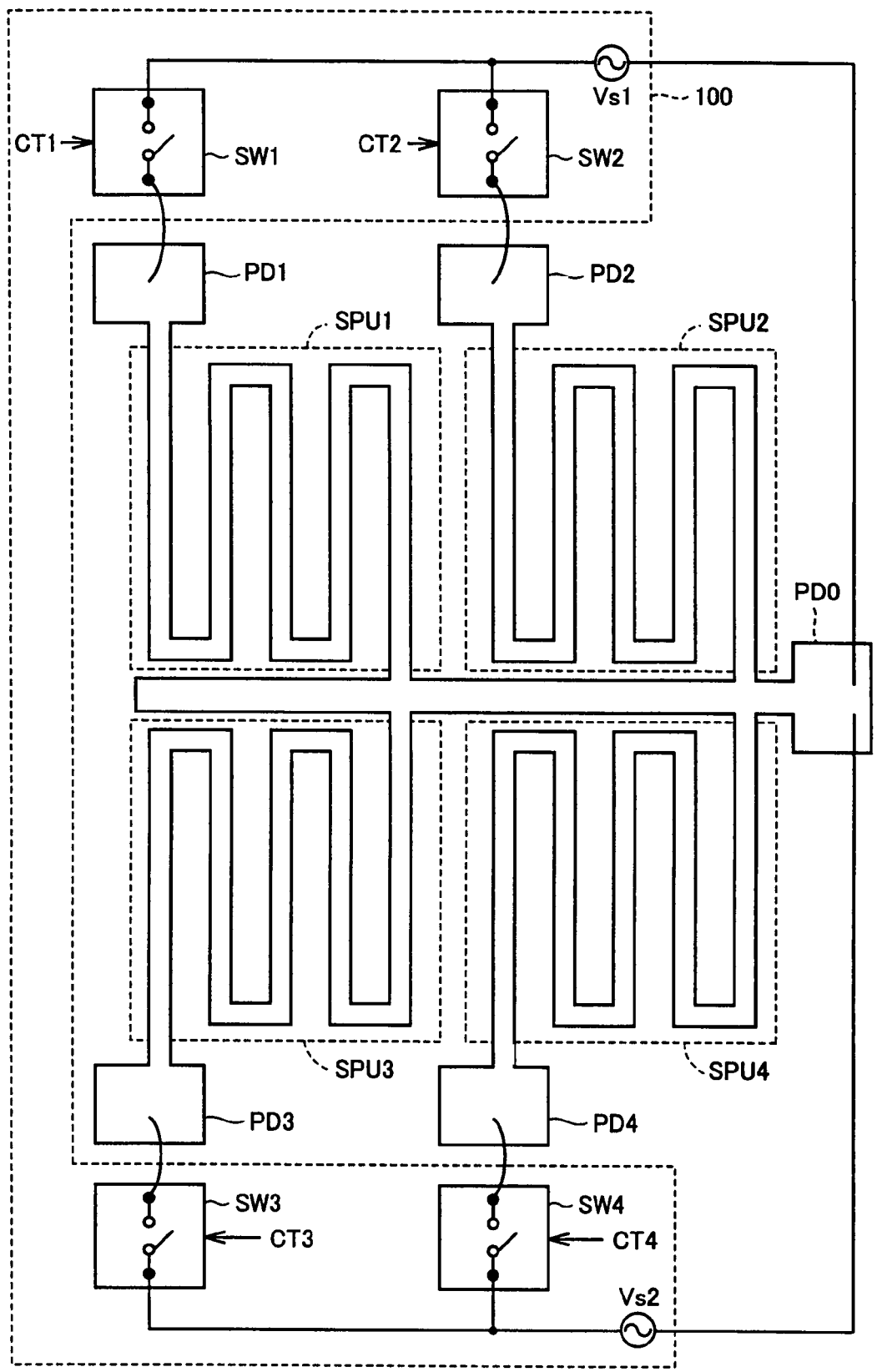
FIG. 27 is a diagram for illustrating a configuration of an internal circuit of speaker unit ARY in accordance with the third embodiment of the present invention.

FIG. 27 is a diagram for illustrating a configuration of an internal circuit of speaker unit ARY in accordance with the third embodiment of the present invention. Herein by way of example a configuration with four sub speaker units will be described. It is, however, not limited thereto and a configuration with more sub speaker units can similarly be discussed.

With reference to FIG. 27, as provided in the present invention by the third embodiment, speaker unit ARY includes sub speaker units SPU1-SPU4 and a switch unit 100.

As provided in the present invention by the third embodiment, switch unit 100 includes switches SW1-SW4 associated with sub speaker units SPU1-SPU4, respectively, and alternate-current power supplies Vs1 and Vs2. Note that while the present example shows switch unit 100 and sub speaker unit SPU provided on a single substrate, it is not limited thereto and of course may have them on different substrates, respectively.

For sub speaker units SPU1, pad PD1 is electrically coupled via switch SW1 with alternate current power supply Vs1 at one electrode and pad PD0 is electrically coupled with alternate current power supply Vs1 at the other electrode. Similarly, for sub speaker unit SPU2, pad PD2 is electrically coupled via switch SW2 with alternate current power supply Vs1 at one electrode and pad PD0 is electrically coupled with alternate current power supply Vs1 at the other electrode. For sub speaker units SPU3, pad PD3 is electrically coupled via switch SW3 with alternate current power supply Vs2 at one electrode and pad PD0 is electrically coupled with alternate current power supply Vs2 at the other electrode. Similarly, for sub speaker units SPU4, pad PD4 is electrically coupled via switch SW4 with alternate current power supply Vs2 at one electrode and pad PD0 is electrically coupled with alternate current power supply Vs2 at the other electrode.

Switches SW1-SW4 operate in response to control signals CT1-CT4, respectively, to conduct to electrically couple their corresponding pads PDs to the alternate current power supplies. More specifically if control unit 20 issues an instruction and speaker control unit 30#a responsively outputs control signal CT1 (for example of the high level), and switch unit 100 receives control signal CT1 (of the high level), switch SW1 conducts to electrically couple alternate current power supply Vs1 and pad PD1 together. As control signal CT1 input to switch unit 100 causes switch SW1 to switch, sub speaker unit SPU1 is selected to output a sound wave as described above. Sub speaker units SPU2-SPU4 are also selected in accordance with a system similar to that for sub speaker unit SPU1 in response to control signals CT2-CT4 received. Note that while herein alternate current power supplies Vs1 and Vs2 are independently provided, a single alternate current power supply may alternately be employed. Note that while in the present example speaker control unit 30#a outputs control signals CT1-CT4 to select switches SW1-SW4, control signals CT1-CT4 may be received externally or from another control circuit and applied.

Furthermore, alternate current power supplies Vs1 and Vs2 may be fixed in frequency or adjusted in frequency for example in response to an instruction provided from speaker control unit 30#a.

Figure 28:
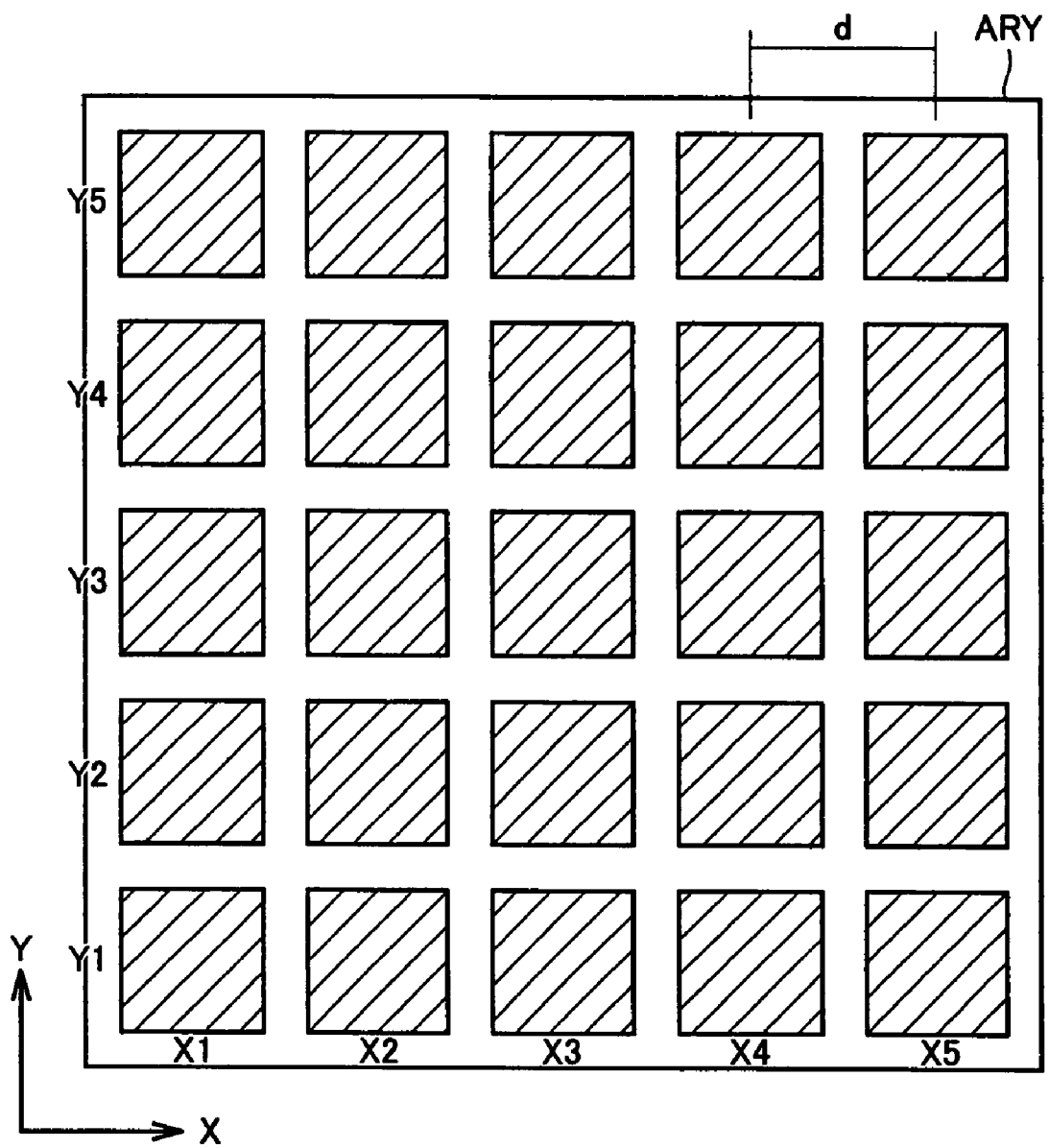
FIG. 28 is a diagram for illustrating how a plurality of sub speaker units SPU are selected in accordance with the third embodiment of the present invention.

FIG. 28 is a diagram for illustrating how a plurality of sub speaker units SPU are selected in the third embodiment of the present invention.

With reference to FIG. 28, herein, switches SWs corresponding to all of sub speaker units SPUs are turned on as described above to cause all of sub speaker units SPU to generate sound waves. Herein, the pitch of adjacent sub speaker units SPUs is set to be pitch d, and the pitch of a plurality of sound sources can be readily set to be pitch d. Note that herein for a direction X addresses X1-X5 are allotted and for a direction Y addresses Y1-Y5 are allotted, and control signal CT corresponding to sub speaker unit SPU of an address in directions X and Y is received and switch SW associated therewith conducts to output a sound wave.

Figure 29:
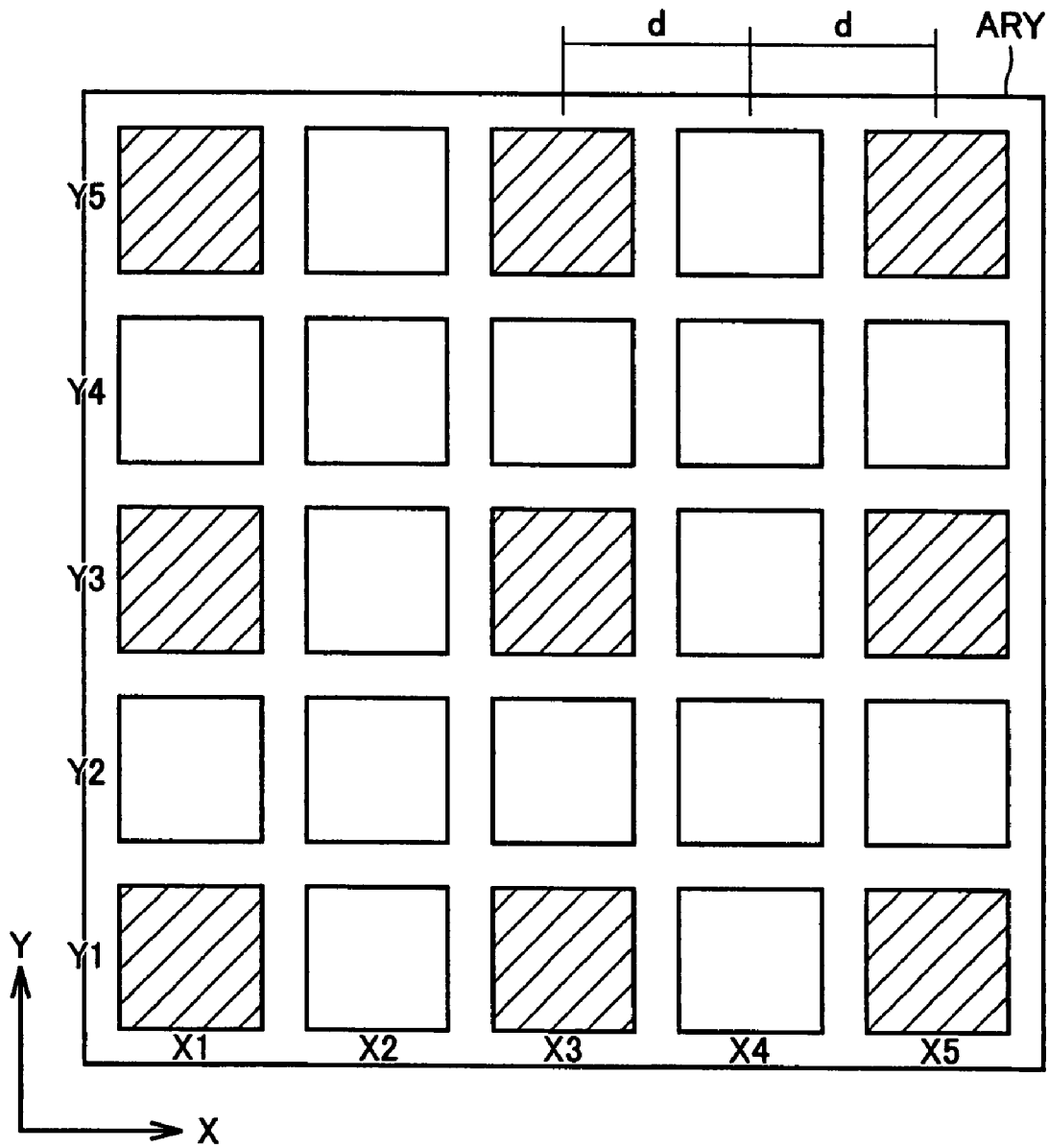
FIG. 29 is another diagram for illustrating how a plurality of sub speaker units SPUs are selected in accordance with the third embodiment of the present invention.

FIG. 29 is another diagram for illustrating how a plurality of sub speaker units SPUs are selected in accordance with the third embodiment of the present invention.

With reference to FIG. 29, the figure shows that sub speaker units SPUs corresponding, as seen in directions X and Y, to addresses (X1, Y1), (X3, Y1), (X5, Y1), (X1, Y3), (X3, Y3), (X5, Y3), (X1, Y5), (X3, Y5), (X5, Y5) have been selected. For example, this can be done by outputting control signals CTs corresponding to sub speaker units SPUs corresponding to the above addresses from speaker control unit 30#, as instructed by control unit 20, to speaker unit ARY.

By such selection, the selected, adjacent sub speaker units SPUs can have a pitch $2d$. A plurality of sound sources can thus readily have pitch $2d$. While hereinabove speaker unit ARY has been described in a configuration allowing a plurality of sound sources to have pitch d or $2d$, speaker unit ARY having a larger number of sub speaker units SPUs may be adjusted in a similar system to provide the plurality of sound sources with pitches $3d$, $4d$, ..., as desired.

This system can eliminate the necessity of following a mechanical system for example employing a manipulator or the like to positionally adjust a plurality of sound sources, and thus allows a simple system to be employed to positionally adjust the sound sources. Furthermore, when the present system turning switch SW on/off to positionally adjust sub speaker unit SPU or a sound source is compared with a mechanical system employed to provide positional adjustment, the former can prevent the sound source from positional displacement and can also positionally adjust the sound source rapidly. Furthermore, the sound source having a significantly small size (settable to be 3 mm or smaller) can be regarded as a point sound source, and the effect of the size of the sound source per se can be neglected and a composite wave can be generated in ideal condition.

Furthermore, the thermal acoustic engine is a non-vibrating sound source. The sound source that itself does not vibrate allows a composite sound field to converge exactly at a location as intended. This allows a test sound wave to be applied accurately to a predetermined portion to inspect it with higher precision. Furthermore, normally, if a sound source other than a non-vibrating sound source is employed, its own vibration must be suppressed and accordingly an anti-vibration mechanism or the like must be introduced. Employing a non-vibrating sound source can eliminate the necessity of introducing such anti-vibration mechanism or the like and also reduce or prevent unwanted vibration other than a test sound wave that would otherwise be transmitted to a movable part of a microstructure, and thus allows the movable part to be inspected with higher precision.

Note that, in fabricating speaker unit ARY on a substrate, not only interconnection but a control unit or a similar device can also be provided on the same substrate, as required. This can reduce interconnection in length and hence reduce interconnection delay as well as layout area.

Furthermore, the control unit can control an individual speaker to output an optimized sound wave, as timed as optimized, having an optimized phase to perform an appropriate inspection.

Third Embodiment in Exemplary Variation

Figure 30:
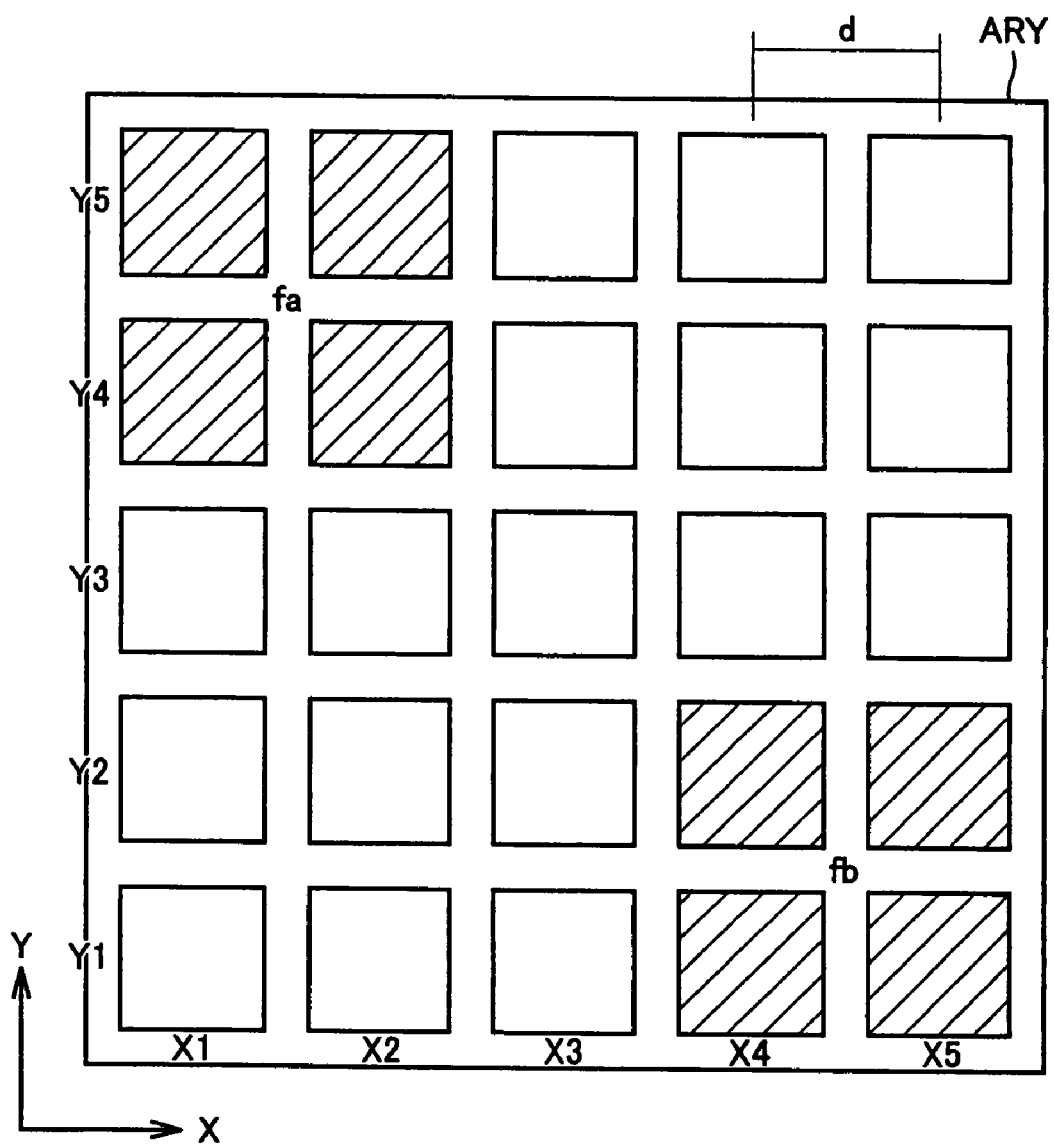
FIG. 30 is another diagram for illustrating how a plurality of sub speaker units SPUs are selected in an exemplary variation of the third embodiment of the present invention.

FIG. 30 is another diagram for illustrating how a plurality of sub speaker units SPUs are selected in an exemplary variation of the third embodiment of the present invention.

While in the above is described a system helping to adjust a plurality of sound sources in pitch to generate a composite test sound wave, hereinafter will be described a system following a simple system to change a position of a test sound wave to change a location at which a composite wave converges.

With reference to FIG. 30, herein, for example four sub speaker units SPUs corresponding, as seen in directions X and Y, to addresses (X1, Y4), (X1, Y5), (X2, Y4), (X2, Y5) are selected and a composite test sound wave is generated that allows a composite sound field maximized for a predetermined location fa of a straight line passing through a center included in a region corresponding to the four sub speaker units for the sake of illustration. In this example if a region corresponding to four sub speaker units SPUs corresponding to (X4, Y1), (X4, Y2), (X5, Y1), (X5, Y2) is for example selected, then a composite test sound wave can similarly be applied that allows a composite sound field maximized for a predetermined location fb of a straight line passing through a center thereof. In other words, a region corresponding to sub speaker unit SPU selected can be shifted to help to shift a position at which a composite sound field is maximized.

Figure 31:
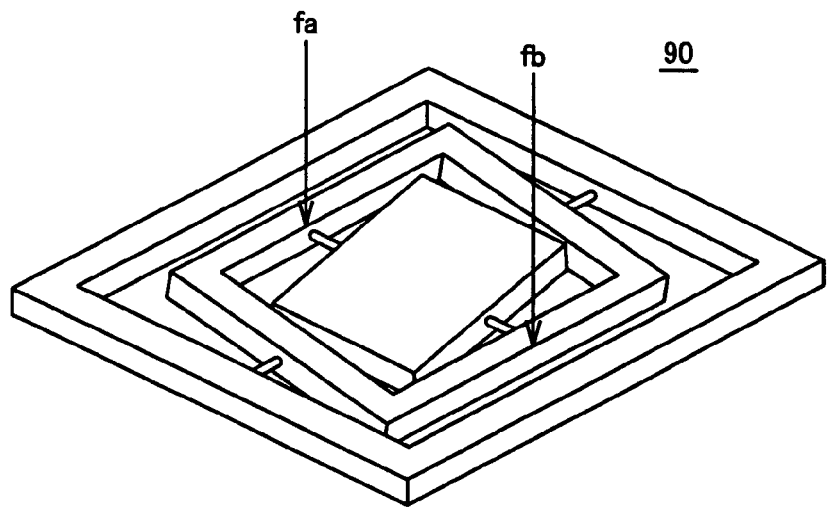
FIG. 31 is a diagram for illustrating a test sound wave applied to torsion mirror 90 at a predetermined portion in accordance with the selection of sub speaker unit SPU as shown in FIG. 30.

FIG. 31 is a diagram for illustrating a test sound wave applied to torsion mirror 90 at a predetermined portion in accordance with the selection of sub speaker unit SPU as shown in FIG. 30.

FIG. 31 shows for example that when four sub speaker units SPUs are selected as described with reference to FIG. 30 and accordingly a test sound wave is applied to torsion mirror 90 at the predetermined (left) portion fa corresponding to one side with respect to the axis of rotation of the rotative frame portion, four sub speaker units SPUs corresponding to another region are selected to shift the test sound wave applied to the predetermined portion fa to the predetermined (right) portion fb corresponding to the other side with respect to the axis of rotation of the rotative frame portion. This can change the direction in which torsion mirror 90 rotates.

Following such a system to change a location at which sub speaker unit SPU is selected can change a location at which a test sound wave is applied or a location at which a composite wave is converged. Note that how sub speaker unit SPU is selected is not limited to the above system and may be selected as desired. Such selection allows a location at which a composite wave is converged to be changed as desired, and a test sound wave to be applied to a location as desired.

Figure 32:
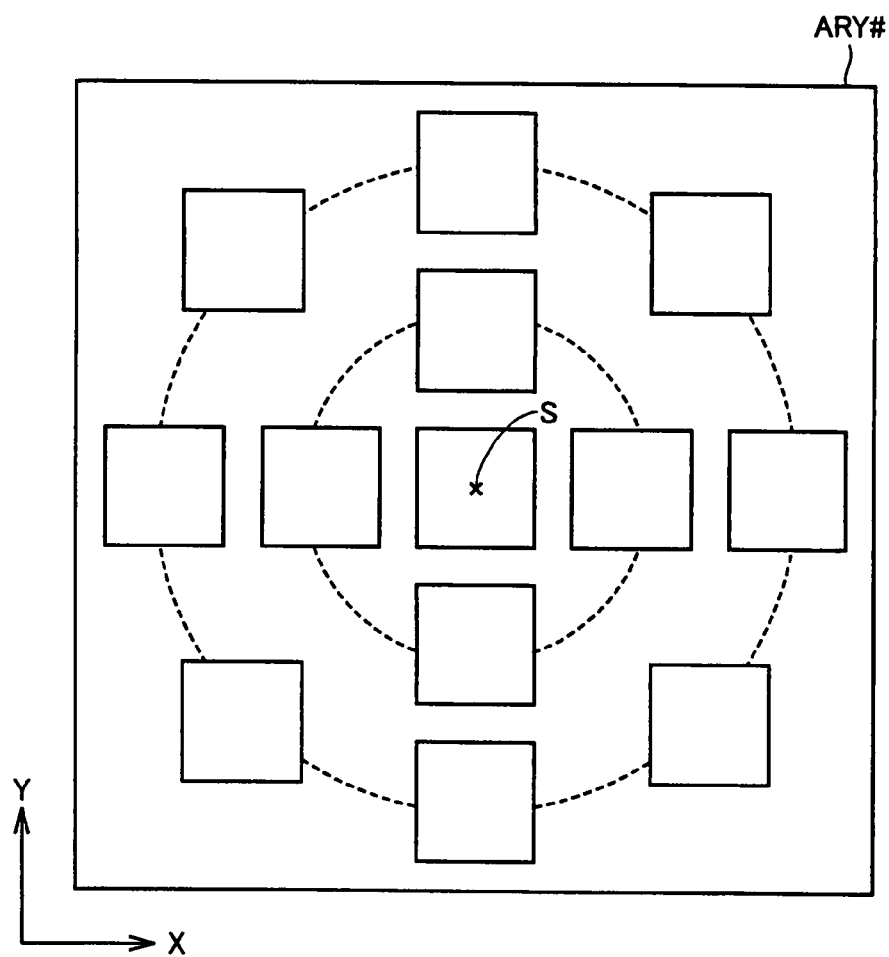
FIG. 32 is a diagram for illustrating a speaker unit ARY#.

Furthermore while the above description has mainly been provided for a plurality of sub speaker units arranged in a matrix, they may alternatively be arranged, for example, concentrically around a center S of speaker unit ARY# shown in FIG. 32 or linearly as a matter of course.

Note that it is not necessary that a plurality of sound sources simultaneously output sound waves. They may be adjusted to output sound waves with a temporal difference to adjust a location for convergence, as described in the second embodiment. Furthermore, modifying a sub speaker unit in wavelength changes a location at which a sound wave allowing a maximized composite sound field is converged. Changing the sub speaker unit in wavelength can thus also adjust the location for convergence.

Note that a program causing a computer to perform a method of for example positionally adjusting a sound source for applying a desired test sound wave, as described above, and the method applying the test sound wave to inspect a microstructure, as described above, may previously be stored in an FD, a CD-ROM, a hard disk or a similar storage medium. In that case, a tester can be provided with a driver device reading the program stored in the storage medium and control unit 20 can receive the program via the driver device to perform the method of for example positionally adjusting the sound source and the method of inspection, as described above. Furthermore, if the computer is networked, the program may be downloaded from a server and control unit 20 may perform the method of for example positionally adjusting the sound source and the method of inspection.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. A microstructure inspection device for evaluating a property of at least one microstructure having a movable part formed on a substrate, comprising:
   a sound wave generation unit for outputting a sound wave to said microstructure in a test, said sound wave generation unit including a plurality of sound sources each configured to output said sound wave, and an adjustment unit for adjusting a composite wave to serve as a predetermined test sound wave, said composite wave being composed of sound waves output from said plurality of sound sources; and
   an evaluation unit for detecting how said movable part of said microstructure moves in response to said test sound wave, and for evaluating said property of said microstructure from how said movable part moves, as detected, wherein
   said plurality of sound sources are arranged to each have a difference in distance to said movable part, the difference being an integer multiple of a wavelength of said sound wave; and
   said microstructure has said movable part at a position allowing a directivity coefficient $R(\theta)=1$ so as to allow a composite sound field from said plurality of sound sources to be maximized.

2. The microstructure inspection device according to claim 1, wherein when said plurality of sound sources include two sound sources, said directivity coefficient is calculated by the following expression:

$R(\theta)=|\cos X|$, and $X=(\pi d/\lambda) \sin \theta$, where d represents a distance between two adjacent ones of said plurality of sound sources, $\lambda$ represents said wavelength of said sound wave, and $\theta$ represents an angle formed by a vector of said test sound wave relative to said movable part and an axis orthogonal to a direction in which said plurality of sound sources are disposed.

3. The microstructure inspection device according to claim 1, wherein when said plurality of sound sources include N sound sources, said directivity coefficient is calculated by the following expression:

$R(\theta)=|\sin(\pi N(d/\lambda) \sin \theta)/N \sin(\pi(d/\lambda) \sin \theta)|$, where d represents a distance between two adjacent ones of said N sound sources, $\lambda$ represents said wavelength of said sound wave, and $\theta$ represents an angle formed by a vector of said test sound wave relative to said movable part and an axis orthogonal to a direction in which said plurality of sound sources are disposed.

4. The microstructure inspection device according to claim 1, wherein said microstructure corresponds to at least one of an acceleration sensor and an angular rate sensor.

5. The microstructure inspection device according to claim 4, wherein said acceleration sensor and said angular rate sensor correspond to a multi-axial acceleration sensor and a multi-axial angular rate sensor, respectively.

6. The microstructure inspection device according to claim 1, wherein:
   said adjustment unit includes a position control unit operative in response to an instruction to control said plurality of sound sources positionally; and
   said sound sources are each movable.

7. The microstructure inspection device according to claim 1, wherein:
   said plurality of sound sources are provided in an array;
   said adjustment unit includes a switch unit for controlling said plurality of sound sources to turn on/off; and
   said plurality of sound sources arranged in said array are selected as said switch unit switches in response to an instruction.

8. The microstructure inspection device according to claim 1, wherein said sound sources are each configured of a thermal acoustic engine including a thermally conductive substrate, a thermal insulation layer formed of a nanocrystalline silicon layer provided on one surface of said substrate, and a heating element receiving a current including an alternate-current component to be electrically driven to exchange heat with air therearound to generate a sound wave.

9. The microstructure inspection device according to claim 1, where said plurality of sound sources are formed on said thermally conductive, single substrate in a semiconductor process collectively.

10. A microstructure inspection device for evaluating a property of at least one microstructure having a movable part formed on a substrate, comprising:
    a sound wave generation unit for outputting a sound wave to said microstructure in a test, said sound wave generation unit including a plurality of sound sources each outputting said sound wave, and an adjustment unit for adjusting a composite wave to serve as a predetermined test sound wave, said composite wave being composed of sound waves output from said plurality of sound sources; and
    an evaluation unit for detecting how said movable part of said microstructure moves in response to said test sound wave, and for evaluating said property of said microstructure from how said movable part moves, as detected, wherein:
    said plurality of sound sources include N sound sources, each outputting said sound wave to arrive at said movable part concurrently, and to do so,
    said plurality of sound sources are driven at times, respectively, each delayed by a $\tau i=Li/c$, to output said sound wave, where $i=0$ to $N-1$, Li represents a distance from each of said N sound sources to said movable part minus a reference distance, and c represents a sonic speed; and
    said movable part is positioned in a manner allowing a composite sound field from said plurality of sound sources to be maximized.

11. A inspection method of evaluating a property of at least one microstructure having a movable part formed on a substrate, comprising the steps of:
- adjusting a composite wave to be a predetermined test sound wave for output, said composite wave being composed of sound waves output from a plurality of sound sources in a test; and
- detecting how said movable part of said microstructure moves in response to said test sound wave, and evaluating said property of said microstructure from how said movable part moves, as detected, wherein:
- said plurality of sound sources are arranged to each have a difference in distance to said movable part, the difference being an integer multiple of a wavelength of said sound wave; and
- said movable part is positioned in a manner allowing a directivity coefficient $R(\theta)=1$ so as to allow a composite sound field from said plurality of sound sources to be maximized.

12. A storage medium having stored therein an inspection program executable by a computer of a microstructure inspecting device for evaluating a property of at least one microstructure having a movable part formed on a substrate, said program causing said computer to perform the steps of:
- adjusting a composite wave to be a predetermined test sound wave for output, said composite wave being composed of sound waves output from a plurality of sound sources in a test; and
- detecting how said movable part of said microstructure moves in response to said test sound wave, and evaluating said property of said microstructure from how said movable part moves, as detected, wherein:
- said plurality of sound sources are arranged to each have a difference in distance to said movable part, said difference being an integer multiple of a wavelength of said sound wave; and
- said movable part is positioned in a manner allowing a directivity coefficient $R(\theta)=1$ so as to allow a composite sound field from said plurality of sound sources to be maximized.

\* \* \* \* \*